(12) United States Patent
Rogers

(10) Patent No.: US 8,889,657 B2
(45) Date of Patent: Nov. 18, 2014

(54) NANOPARTICLE PEG MODIFICATION WITH H-PHOSPHONATES

(75) Inventor: Thomas E. Rogers, Ballwin, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 104 days.

(21) Appl. No.: 13/599,819

(22) Filed: Aug. 30, 2012

(65) Prior Publication Data

US 2013/0066086 A1    Mar. 14, 2013

Related U.S. Application Data

(60) Provisional application No. 61/529,694, filed on Aug. 31, 2011.

(51) Int. Cl.
*A61K 47/48*        (2006.01)

(52) U.S. Cl.
CPC ..... *A61K 47/48084* (2013.01); *A61K 47/48815* (2013.01); *A61K 47/48215* (2013.01); *Y10S 977/773* (2013.01); *Y10S 977/836* (2013.01)
USPC ............. 514/76; 514/740; 558/158; 558/160; 558/161; 558/166; 977/773; 977/836

(58) Field of Classification Search
USPC ............ 514/76, 740; 558/158, 160, 161, 166; 977/773, 836
See application file for complete search history.

(56) References Cited

U.S. PATENT DOCUMENTS

| 2005/0234021 A1* | 10/2005 | Petasis | 514/79 |
| 2007/0154537 A1* | 7/2007 | Greb et al. | 424/450 |
| 2012/0059147 A1* | 3/2012 | Komiyama et al. | 530/322 |

FOREIGN PATENT DOCUMENTS

| EP | 2 221 372 A1 | 8/2010 | | |
| GB | 2 113 861 A | 8/1983 | | |
| WO | 2005/070952 A1 | 8/2005 | | |
| WO | 2011/097563 A1 | 8/2011 | | |
| WO | WO2011/097563 A1 * | 8/2011 | ............. | A61K 9/127 |
| WO | 2011/137135 A1 | 11/2011 | | |

OTHER PUBLICATIONS

Choi et al., "Design of surface-modified poly(d, I-lactide-co-glycolide) nanoparticles for targeted drug delivery to bone," Journal of Controlled Release, Aug. 2007, 122(1-):24-30.*
Barouda et al., "Barium Sulfate Crystallization in the Presence of Variable Chain Length Aminomethylenetetraphosphonates and Cations (Na+ or Zn2+)", 2007, Crystal Growth & Design, 7(2):321-327.*
Balaraman et al., "Hydrophosphonylation of activated alkenes and alkynes via fluoride ion activation in ionic liquid medium," Tetrahedron, Sep. 2009, vol. 65, No. 36, pp. 7603-7610.
Barouda et al., "Barium Sulfate Crystallization in the Presence of Variable Chain Length Aminomethylenetetraphosphonates and Cations (Na+ or Zn+)," Crystal Growth and Design, Jan. 2007, vol. 7, No. 2, pp. 321-327.
Choi et al., "Design of surface-modified poly(d, i-lactide-co-glycolide) nanoparticles for targeted drug delivery to bone," Journal of Controlled Release, Aug. 2007, vol. 122, No. 1, pp. 24-30.
PCT Communication Relating to the Results of the Partial International Search, Mailing Date Nov. 7, 2012, PCT application No. PCT/US2012/053197, 3 pages.

* cited by examiner

*Primary Examiner* — Jane C Oswecki

(57) ABSTRACT

The present invention provides phosphonate conjugates and methods of preparing the phosphonate conjugates so as to allow, for example, improved methods and compounds for modifying the surface of a nanoparticle to increase in vivo circulation times and targeted delivery performance.

20 Claims, 5 Drawing Sheets n=0
$R^1$ = PEG100 – PEG10000
$R^3, R^4$ = $C_1$–$C_{20}$ alkyl n=1, $L^2$=a bond
$R^1$=PEG100 – PEG10000
$R^2$=methyl
$R^3, R^4$=$C_1$–$C_{20}$ alkyl

NANOPARTICLE PEG MODIFICATION WITH H-PHOSPHONATES

CROSS-REFERENCES TO RELATED APPLICATIONS

This application claims the benefit of priority to U.S. Provisional Application Ser. No. 61/529,694, the entire content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Currently, the majority of therapeutic and diagnostic agents are administered to patients systemically. Unfortunately, current delivery methods can have several disadvantages including reduced efficacy of therapeutics as well as side effects due to, for example, drug activation at non-target sites in a patient. In an effort to address some of these drawbacks, targeting delivery of nanoparticles associated with diagnostic and therapeutic agents presents a promising new mode of drug delivery.

Under certain circumstances, however, the nanoparticles can be rejected by a patient's immune system and processed before the nanoparticle can reach a target for delivery of a drug. To address these problems, surfaces of nanoparticles can be modified. For example, nanoparticles, such as liposomes, are commonly modified to incorporate polyethylene glycol (PEG) groups on their surface to enhance in vivo performance. Generally, there are two common approaches employed to achieve liposomal PEG modification. One approach includes combining lipid-PEG molecules to form liposomal formulations under mechanical means, e.g., extrusion. In another approach, liposomes can be preassembled and subsequently treated with a properly disposed PEG-lipid under conditions where the lipid can insert in the liposome bilayer, thereby forming a liposome with PEG attached to the liposome surface.

While there have been some recent advancements in developing targeted drug delivery methods, there is still a need for further improvements. For example, current approaches for modifying nanoparticles provide only a limited number of modifications that can be made to a nanoparticle. The present invention addresses these and other needs.

BRIEF SUMMARY OF THE INVENTION

The present invention provides phosphonate conjugates and methods of preparing the phosphonate conjugates so as to allow, for example, improved methods and compounds for modifying the surface of a nanoparticle to increase in vivo circulation times and targeted delivery performance.

In one aspect of the invention, the phosphonate conjugates of the present invention can include a compound of the formula:

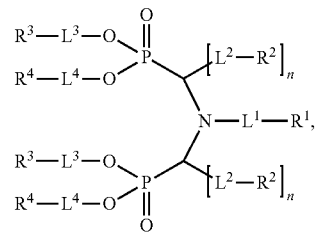

wherein each of $R^1$, $R^2$, $R^3$, $R^4$, $L^1$, $L^2$, $L^3$ and $L^4$ are described in more detail below.

In another aspect, the present invention includes a compound of the formula:

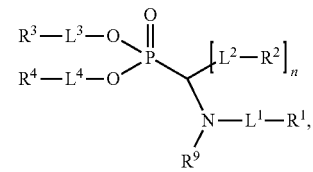

wherein $R^1$, $R^2$, $R^3$, $R^4$, $R^9$, $L^1$, $L^2$, $L^3$ and $L^4$ are described in more detail below.

In yet another aspect, the present invention includes a method of preparing a phosphonate conjugate, the method comprising: combining a primary amine compound having the formula: $H_2N(L^1)\text{-}(R^1)$, a carbonyl compound having the formula: $O\!=\!C[(L^2)\text{-}(R^2)]_n$, and a H-phosphonate compound having the formula:

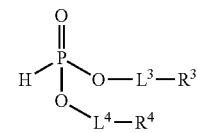

under conditions sufficient to form the phosphonate conjugate having the formula:

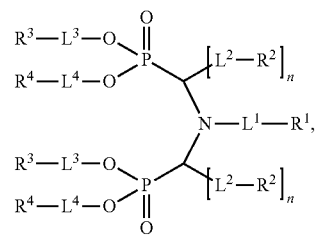

wherein the phosphonate conjugates, primary amine compounds, carbonyl compounds, and H-phosphonate compounds are described in more detail below.

In yet another aspect, the present invention includes a method of preparing a phosphonate conjugate, the method comprising: combining a secondary amine compound having the formula: $HN[(L^1)\text{-}(R^1)](R^9)$, a carbonyl compound having the formula: $O\!=\!C[(L^2)\text{-}(R^2)]_n$, and a H-phosphonate compound having the formula:

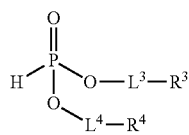

under conditions sufficient to form the phosphonate conjugate having the formula:

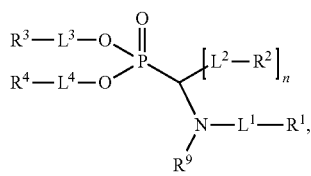

wherein the phosphonate conjugates, secondary amine compounds, carbonyl compounds, and H-phosphonate compounds are described in more detail below.

The phosphonate conjugates of the present invention and their methods of making provide a number of unique aspects to the areas of drug delivery and diagnostic imaging. For example, the present invention provides robust and simple methods for making compounds that can facilitate transforming nanoparticles into stealth nanoparticles that can be used for targeted drug delivery. In certain instances, the phosphonate conjugates provide unique capability to increase the density of stealth agents on the surface of a nanoparticle and can, therefore, allow for additional flexibility in using different stealth agents that may not be as effective at lower densities. In addition, the phosphonate conjugates can be produced in a fashion to provide additional stability to present stealth agents or other components, e.g., targeting agents, on the surface of a nanoparticle. Among other advantages, the phosphonate conjugates can incorporate positively- and/or negatively-charged groups to facilitate modification of the surface characteristics of nanoparticles. The flexibility in making modified nanoparticles can, also, allow for tailored nanoparticles for specific therapeutic and/or diagnostic applications that can have long in vivo half-lives after administration to a patient.

A further understanding of the nature and advantages of the present invention can be realized by reference to the remaining portions of the specification and the drawings.

DETAILED DESCRIPTION OF THE INVENTION

I. Definitions

Figure 1:
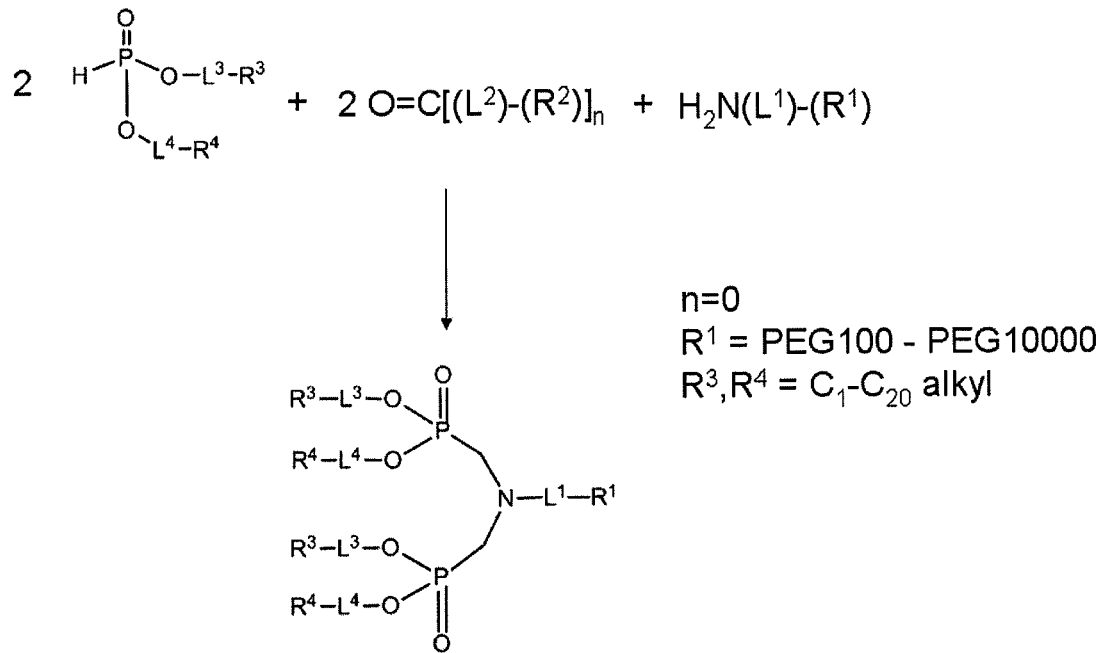
FIG. 1 depicts an example synthetic method for producing a phosphonate conjugate of the present invention.

As used herein, the symbol "—" means a single bond, "═" means a double bond, "≡" means a triple bond, and "====" means a single or double bond.

As used herein, the term "alkyl," by itself or as part of another substituent, means, unless otherwise stated, a straight or branched chain hydrocarbon radical, having the number of carbon atoms designated (i.e., $C_{10-24}$ means ten to twenty-four carbons). In some embodiments, alkyl groups can range from one to thirty-six carbons. In certain embodiments, alkyl groups can range from one to ten carbons or one to twenty carbons. In some embodiments, the alkyl groups can be saturated or unsaturated, as well as substituted or unsubstituted.

As used herein, the term "substituted" refers to a group that is bonded to a parent molecule or group. For example, an alkyl group having a cyano substituent is a cyano-substituted alkyl group. Suitable substituents include, but are not limited to, halo, cyano, alkyl, amino, hydroxy, alkoxy, and amido.

As used herein, the term "H-phosphonate compound" refers to compounds having the general formula of H—P(O)$(OL^3-R^3)(OL^4-R^4)$ and is further described herein.

As used herein, the term "primary amine compound" refers generally to compounds having the general formula $H_2N(L^1)-(R^1)$ and is further described herein.

As used herein, the term "secondary amine compound" refers generally to compounds having the general formula $HN[(L^1)-(R^1)](R^9)$ and is further described herein.

As used herein, the term "carbonyl compound" refers generally to compounds having the general formula $O=C[(L^2)-(R^2)]_n$ and is further described herein.

As used herein, the term "targeted delivery composition" refers to a composition of a nanoparticle attached to a phosphonate conjugate of the present invention, the specifics of which are described further herein. The compositions of the present invention can be used as therapeutic compositions, as diagnostic compositions, or as both therapeutic and diagnostic compositions. In certain embodiments, the compositions can be targeted to a specific target within a subject or a test sample, as described further herein.

As used herein, the term "nanoparticle" refers to particles of varied size, shape, type and use, which are further described herein. As will be appreciated by one of ordinary skill in the art, the characteristics of the nanoparticles, e.g., size, can depend on the type and/or use of the nanoparticle as well as other factors generally well known in the art. In general, nanoparticles can range in size from about 1 nm to about 1000 nm. In other embodiments, nanoparticles can range in size from about 10 nm to about 200 nm. In yet other embodiments, nanoparticles can range in size from about 50 nm to about 150 nm. In certain embodiments, the nanoparticles are greater in size than the renal excretion limit, e.g., greater than about 6 nm in diameter. In other embodiments, the nanoparticles are small enough to avoid clearance from the bloodstream by the liver, e.g., smaller than 1000 nm in diameter. Nanoparticles can include spheres, cones, spheroids, and other shapes generally known in the art. Nanoparticles can be hollow (e.g., solid outer core with a hollow inner core) or solid or be multilayered with hollow and solid layers or a variety of solid layers. For example, a nanoparticle can include a solid core region and a solid outer encapsulating region, both of which can be cross-linked. Nanoparticles can be composed of one substance or any combination of a variety of substances, including lipids, polymers, magnetic materials, or metallic materials, such as silica, gold, iron oxide, and the like. Lipids can include fats, waxes, sterols, cholesterol, fat-soluble vitamins, monoglycerides, diglycerides, phospholipids, sphingolipids, glycolipids, cationic or anionic lipids, derivatized lipids, cardiolipin and the like. Polymers can include block copolymers generally, poly(lactic acid), poly(lactic-co-glycolic acid), polyethylene glycol, acrylic polymers, cationic polymers, as well as other polymers known in the art for use in making nanoparticles. In some embodiments, the polymers can be biodegradable and/or biocompatible. Nanoparticles can include a liposome, a micelle, a lipoprotein, a lipid-coated bubble, a block copolymer micelle, a polymersome, a niosome, a quantum dot, an iron oxide particle, a gold particle, a dendrimer, or a silica particle. In certain embodiments, a lipid monolayer or bilayer can fully or partially coat a nanoparticle composed of a material capable of being coated by lipids, e.g., polymer nanoparticles. In some embodiments, liposomes can include multilamellar vesicles (MLV), large unilamellar vesicles (LUV), and small unilamellar vesicles (SUV).

As used herein, the term "therapeutic agent" refers to a compound or molecule that, when present in an effective amount, produces a desired therapeutic effect on a subject in need thereof. The present invention contemplates a broad range of therapeutic agents and their use in conjunction with the nanoparticles and phosphonate conjugates, as further described herein.

As used herein, the term "diagnostic agent" refers to a component that can be detected in a subject or test sample and is further described herein.

As used herein, the term "linking group" refers to part of a phosphonate conjugate that links portions of the conjugate. For example, a linking group, $L^3$, can link $R^3$ (e.g., an attachment component) to an oxygen bound to the phosphorous of the phosphonate conjugate. Depending on the phosphonate conjugate being prepared and the properties desired for the compound, the linking group can be assembled from readily available monomeric components to achieve an appropriate separation of targeting agent and other portions of a phosphonate conjugate that may, e.g., be attached to a nanoparticle.

As used herein, the term "targeting agent" refers to a molecule that is specific for a target. In certain embodiments, a targeting agent can include a small molecule mimic of a target ligand (e.g., a peptide mimetic ligand), a target ligand (e.g., an RGD peptide containing peptide or folate amide), or an antibody or antibody fragment specific for a particular target. Targeting agents can bind a wide variety of targets, including targets in organs, tissues, cells, extracellular matrix components, and/or intracellular compartments that can be associated with a specific developmental stage of a disease. In some embodiments, targets can include cancer cells, particularly cancer stem cells. Targets can further include antigens on a surface of a cell, or a tumor marker that is an antigen present or more prevalent on a cancer cell as compared to normal tissue. In certain embodiments, a targeting agent can further include folic acid derivatives, B-12 derivatives, integrin RGD peptides, RGD mimetics (Temming, K. et al., Drug Resistance Updates 8:381-402 (2005); Liu, S., Mol. Pharm. 3(5): 472-87 (2006)), NGR derivatives, somatostatin derivatives or peptides that bind to the somatostatin receptor, e.g., octreotide and octreotate, and the like. In some embodiments, a targeting agent can be an aptamer—which is composed of nucleic acids (e.g., DNA or RNA), or a peptide and which binds to a specific target. A targeting agent can be designed to bind specifically or non-specifically to receptor targets, particularly receptor targets that are expressed in association with tumors. Examples of receptor targets include, but are not limited to, MUC-1, EGFR, Claudin 4, MUC-4, CXCR4, CCR7, FOL1R, somatostatin receptor 4, Erb-B2 (erythroblastic leukaemia oncogene homologue 2) receptor, CD44 receptor, and VEGF receptor-2 kinase.

As used herein, the term "stealth agent" refers to a molecule that can modify the surface properties of a nanoparticle and is further described herein.

As used herein, the term "tetrapodal presentation component" refers to a molecule having the general formula:

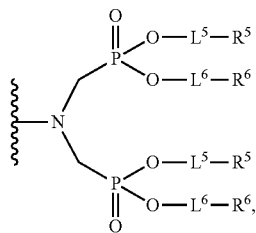

wherein $L^5$, $L^6$, $R^5$ and $R^6$ are further described herein. In some embodiments, each of $L^5$ and $L^6$ is independently selected from the group consisting of a bond and a linking group; and each $R^5$ and $R^6$ is independently selected from the group consisting of an $C_1$-$C_{36}$ alkyl, a targeting agent, a diagnostic agent, and a stealth agent. In some embodiments, $R^5$ and/or $R^6$ can be hydrogen.

As used herein, the term "embedded in" refers to the location of an agent on or in the vicinity of the surface of a nanoparticle. Agents embedded in a nanoparticle can, for example, be located within a bilayer membrane of a liposome or located within an outer polymer shell of a nanoparticle so as to be contained within that shell.

As used herein, the term "encapsulated in" refers to the location of an agent that is enclosed or completely contained within the inside of a nanoparticle. For liposomes, for example, therapeutic and/or diagnostic agents can be encapsulated so as to be present in the aqueous interior of the liposome. Release of such encapsulated agents can then be triggered by certain conditions intended to destabilize the liposome or otherwise effect release of the encapsulated agents.

As used herein, the term "tethered to" refers to attachment of one component to another component so that one or more of the components has freedom to move about in space. In certain exemplary embodiments, an attachment component can be tethered to a nanoparticle so as to freely move about in solution surrounding the nanoparticle. In some embodiments, an attachment component can be tethered to the surface of a nanoparticle, extending away from the surface.

As used herein, the term "lipid" refers to lipid molecules that can include fats, waxes, sterols, cholesterol, cholesterol derivatives, fat-soluble vitamins, monoglycerides, diglycerides, $C_8$-$C_{36}$ alkyl, phospholipids, sphingolipids, glycolipids, cationic or anionic lipids, derivatized lipids, and the like. Lipids can form micelles, monolayers, and bilayer membranes. In certain embodiments, the lipids can self-assemble into liposomes. In other embodiments, the lipids can coat a surface of a nanoparticle as a monolayer or a bilayer.

As used herein, the term "aptamer" refers to a non-naturally occurring oligonucleotide (typically 20-200 nucleotides) that specifically binds to a particular target. "Non-naturally occurring" encompasses non-naturally occurring sequences of natural nucleotides (A, T, C, G, U), as well as oligonucleotides with non-naturally occurring or modified nucleotides. For example, "Spiegelmers®" are aptamers with mirror image nucleic acids, i.e., in the L chiral configuration instead of the naturally occurring D configuration. Aptamers can form unique three-dimensional structures via intramolecular interactions, and/or change structure upon binding to a target, e.g., via an induced-fit mechanism from a primary or secondary structure. Aptamer binding to the target is not mediated by traditional complementary nucleic acid hybridization, e.g., double or triple helix formation, though portions of the aptamer may participate in such hybridization. For example, aptamers commonly form intramolecular hairpin structures and other three dimensional structures. Aptamers can be selected according to any method or combination of methods. Systematic Evolution of Ligands by Exponential Enrichment (SELEX™), or a variation thereof, is commonly used in the field. The basic SELEX™ process is described e.g., in U.S. Pat. No. 5,567,588. A number of variations on the basic method can also be used, e.g., in vivo SELEX™, as described in US Appl. No. 2010015041. MONOLEX™ is another selection process described, e.g., in Nitsche et al. (2007) *BMC Biotechnology* 7:48 and WO02/29093. In vivo selection using nucleic acid libraries injected into tumor cells is also possible (see, e.g., Mi et al., (2010) *Nat. Chem. Biol.* 1:22). Aptamers for use in the present invention can be designed to bind to a variety of targets, including but not limited to MUC-1, EGFR, Claudin 4, MUC-4, CXCR4, CCR7, FOL1R, somatostatin receptor 4, Erb-B2 (erythroblastic leukaemia oncogene homologue 2) receptor, CD44 receptor, VEGF receptor-2 kinase, and nucleolin.

As used herein, the term "subject" refers to any mammal, in particular human, at any stage of life.

As used herein, the terms "administer," "administered," or "administering" refers to methods of administering the targeted delivery compositions of the present invention. The targeted delivery compositions of the present invention can be administered in a variety of ways, including topically, parenterally, intravenously, intradermally, intramuscularly, colonically, rectally or intraperitoneally. Parenteral administration and intravenous administration are the preferred methods of administration. The targeted delivery compositions can also be administered as part of a composition or formulation.

As used herein, the terms "treating" or "treatment" of a condition, disease, disorder, or syndrome includes (i) inhibiting the disease, disorder, or syndrome, i.e., arresting its development; and (ii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the term "formulation" refers to a mixture of components for administration to a subject. Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. The formulations of a targeted delivery composition can be presented in unit-dose or multi-dose sealed containers, such as ampoules and vials. A targeted delivery composition, alone or in combination with other suitable components, can be made into aerosol formulations (i.e., they can be "nebulized") to be administered via inhalation through the mouth or the nose. Aerosol formulations can be placed into pressurized acceptable propellants, such as dichlorodifluoromethane, propane, nitrogen, and the like. Suitable formulations for rectal administration include, for example, suppositories, which comprises an effective amount of a targeted delivery composition with a suppository base. Suitable suppository bases include natural or synthetic triglycerides or paraffin hydrocarbons. In addition, it is also possible to use gelatin rectal capsules which contain a combination of the targeted delivery composition with a base, including, for example, liquid triglycerides, polyethylene glycols, and paraffin hydrocarbons. In certain embodiments, formulations can be administered topically or in the form of eye drops.

Embodiments of the Invention

II. General

The phosphonate conjugates of the present invention and their methods of making provide a number of unique aspects to the areas of drug delivery and diagnostic imaging. For example, the present invention provides robust and simple methods for making compounds that can facilitate transforming nanoparticles into stealth nanoparticles that can be used for targeted drug delivery. In certain instances, the phosphonate conjugates provide unique capability to increase the density of stealth agents on the surface of a nanoparticle and can, therefore, allow for additional flexibility in using different stealth agents that may not be as effective at lower densities. In addition, the phosphonate conjugates can be produced in a fashion to provide additional stability to present stealth agents or other components, e.g., targeting agents, on the surface of a nanoparticle.

Furthermore, the phosphonate compounds can be integrated into nanoparticles by a variety of ways. For example, a H-phosphonate compound can be produced using methods described herein and then integrated with a nanoparticle such that the H-phosphonate compound is on the surface of the nanoparticle. The H-phosphonate compounds can, for example, be integrated with a nanoparticle by incorporating the H-phosphonate compounds prior to making the nanoparticle. In other instances, a nanoparticle can be produced and the H-phosphonate compounds can be attached to the surface of the nanoparticle, thereby modifying the surface of the nanoparticle. The flexibility in making modified nanoparticles can, for example, allow for tailored nanoparticles for specific therapeutic and/or diagnostic applications that can also have long in vivo half-lives after administration to a patient.

III. Phosphonate Conjugates

In one aspect, the compounds of the present invention can include a compound of the formula:

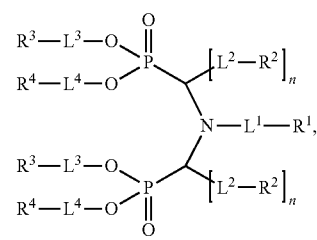

wherein each $L^1$, $L^2$, $L^3$ and $L^4$ is independently selected from the group consisting of a bond and a linking group; $R^1$ is selected from the group consisting of a nanoparticle, an attachment component, a targeting agent, a diagnostic agent, a stealth agent, and a tetrapodal presentation component; each $R^2$ is independently selected from the group consisting of a stealth agent, $C_1$-$C_{10}$ alkyl, a carboxylic acid or ester, a phosphonic acid or ester, a sulfonic acid or ester, and a hydroxy; each $R^3$ and $R^4$ is independently selected from the group consisting of H, a nanoparticle, an attachment component, a targeting agent, a diagnostic agent, and a stealth agent, wherein at least one of $R^3$ or $R^4$ is other than H; and n is an integer of from 0 to 2.

In another aspect, the compounds of the present invention can include a compound of the formula:

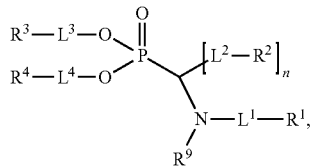

wherein each $L^1$, $L^2$, $L^3$ and $L^4$ is independently selected from the group consisting of a bond and a linking group; $R^1$ is selected from the group consisting of a nanoparticle, an attachment component, a targeting agent, a diagnostic agent and a stealth agent; $R^2$ is independently selected from the group consisting of a stealth agent, $C_1$-$C_{10}$ alkyl, a carboxylic acid or ester, a phosphonic acid or ester, a sulfonic acid or ester, and a hydroxy; each $R^3$ and $R^4$ is independently selected from the group consisting of H, a nanoparticle, an attachment component, a targeting agent, a diagnostic agent, and stealth agent, wherein at least one of $R^3$ or $R^4$ is other than H; $R^9$ is a $C_1$-$C_{10}$ alkyl group; and n is an integer from 0 to 2.

Nanoparticles

A wide variety of nanoparticles can be used in the present invention. As will be appreciated by one of ordinary skill in the art, the characteristics of the nanoparticles, e.g., size, can depend on the type and/or use of the nanoparticle as well as other factors generally well known in the art. Suitable particles can be spheres, spheroids, flat, plate-shaped, tubes, cubes, cuboids, ovals, ellipses, cylinders, cones, or pyramids. Suitable nanoparticles can range in size of greatest dimension (e.g., diameter) from about 1 nm to about 1000 nm, from about 10 nm to about 200 nm, and from about 50 nm to about 150 nm.

Suitable nanoparticles can be made of a variety of materials generally known in the art. In some embodiments, nanoparticles can include one substance or any combination of a variety of substances, including lipids, polymers, or metallic materials, such as silica, gold, iron oxide, and the like. Examples of nanoparticles can include but are not limited to a liposome, a micelle, a lipoprotein, a lipid-coated bubble, a block copolymer micelle, a polymersome, a niosome, an iron oxide particle, a gold particle, a silica particle, a dendrimer, or a quantum dot.

In some embodiments, the nanoparticles are liposomes composed partially or wholly of saturated or unsaturated lipids. Suitable lipids can include but are not limited to fats, waxes, sterols, cholesterol, cholesterol derivatives, fat-soluble vitamins, monoglycerides, diglycerides, phospholipids, sphingolipids, glycolipids, derivatized lipids, and the like. In some embodiments, suitable lipids can include amphipathic, neutral, non-cationic, anionic, cationic, or hydrophobic lipids. In certain embodiments, lipids can include those typically present in cellular membranes, such as phospholipids and/or sphingolipids. Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (PI). Suitable sphingolipids include but are not limited to sphingosine, ceramide, sphingomyelin, cerebrosides, sulfatides, gangliosides, and phytosphingosine. Other suitable lipids can include lipid extracts, such as egg PC, heart extract, brain extract, liver extract, and soy PC. In some embodiments, soy PC can include Hydro Soy PC (HSPC). Cationic lipids include but are not limited to N,N-dioleoyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA). Non-cationic lipids include but are not limited to dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. In certain embodiments, the lipids can include derivatized lipids, such as PEGlyated lipids. Derivatized lipids can include, for example, DSPE-PEG$_{2000}$, cholesterol-PEG$_{2000}$, DSPE-polyglycerol, or other derivatives generally well known in the art.

Any combination of lipids can be used to construct a nanoparticle, such as a liposome. In certain embodiments, the lipid composition of a liposome, can be tailored to affect characteristics of the liposomes, such as leakage rates, stability, particle size, zeta potential, protein binding, in vivo circulation, and/or accumulation in tissue, such as a tumor, liver, spleen or the like. For example, DSPC and/or cholesterol can be used to decrease leakage from the liposomes. Negatively or positively lipids, such as DSPG and/or DOTAP, can be included to affect the surface charge of a liposome. In some embodiments, the liposomes can include about ten or fewer types of lipids, or about five or fewer types of lipids, or about three or fewer types of lipids. In some embodiments, the molar percentage (mol %) of a specific type of lipid present typically comprises from about 0% to about 10%, from about 10% to about 30%, from about 30% to about 50%, from about 50% to about 70%, from about 70% to about 90%, from about 90% to 100% of the total lipid present in a nanoparticle, such as a liposome. The lipids described herein can be included in a liposome, or the lipids can be used to coat a nanoparticle of the invention, such as a polymer nanoparticle. Coatings can be partially or wholly surrounding a nanoparticle and can include monolayers and/or bilayers.

In other embodiments, a portion or all of a nanoparticle can include a polymer, such as a block copolymer or other polymers known in the art for making nanoparticles. In some embodiments, the polymers can be biodegradable and/or biocompatible. Suitable polymers can include but are not limited to polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, and combinations thereof. In some embodiments, exemplary particles can include shell cross-linked knedels, which are further described in the following references: Becker et al., U.S. application Ser. No. 11/250,830; Thurmond, K. B. et al., *J. Am. Chem. Soc.*, 119 (28) 6656 (1997)); Wooley, K. L., *Chem. Eur. J.*, 3 (9): 1397-1399 (1997); Wooley, K. L., *J. Poly. Sci.: Part A: Polymer Chem.*, 38: 1397-1407 (2000). In other embodiments, suitable particles can include poly(lactic co-glycolic acid) (PLGA) (Fu, K. et al., *Pharm Res.*, 27:100-106 (2000).

In yet other embodiments, the nanoparticles can be partially or wholly composed of materials that are metallic in nature, such as silica, gold, iron oxide, and the like. In some embodiments, the silica particles can be hollow, porous, and/or mesoporous (Slowing, I. I., et al., *Adv. Drug Deliv. Rev.*, 60 (11):1278-1288 (2008)). Gold particles are generally known in the art, as provided by the following exemplary reference: Bhattacharya, R. & Mukherjee, P., *Adv. Drug Deliv. Rev.*, 60(11): 1289-1306 (2008)). Iron oxide particles or quantum dots can also be used and are well-known in the art (van Vlerken, L. E. & Amiji, M. M., *Expert Opin. Drug Deliv.*, 3(2): 205-216 (2006)). The nanoparticles also include but are not limited to viral particles and ceramic particles.

Attachment to a Nanoparticle

In certain embodiments, the attachment component can include a functional group that can be used to covalently attach the attachment component to a reactive group present on the nanoparticle. The functional group can be located anywhere on the attachment component, such as, e.g., the terminal position of an alkylene or heteroalkylene moiety. A wide variety of functional groups are generally known in the art and can be reacted under several classes of reactions, such as but not limited to nucleophilic substitutions (e.g., reactions of amines and alcohols with acyl halides or active esters), electrophilic substitutions (e.g., enamine reactions) and additions to carbon-carbon and carbon-heteroatom multiple bonds (e.g., Michael reaction or Diels-Alder addition). These and other useful reactions are discussed in, for example, March, *Advanced Organic Chemistry*, 3rd Ed., John Wiley & Sons, New York, 1985; and Hermanson, *Bioconjugate Techniques*, Academic Press, San Diego, 1996. Suitable functional groups can include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido groups; (e) aldehyde or ketone groups such that subsequent derivatization is possible via formation of carbonyl derivatives such as, for example, imines, hydrazones, semicarbazones or oximes, or via such reactions as Grignard addition or alkyllithium addition; (f) sulfonyl halide groups for subsequent reaction with amines, for example, to form sulfonamides; (g) thiol groups, which can be converted to disulfides or reacted with acyl halides; (h) amine or sulfhydryl groups, which can be, for example, acylated, alkylated or oxidized; (i) alkenes, which can undergo, for example, cycloadditions, acylation, Michael addition, etc; and (j) epoxides, which can react with, for example, amines and hydroxyl compounds. In some embodiments, click chemistry-based platforms can be used to attach the attachment component to a nanoparticle (Kolb, H. C., M. G. Finn and K. B. Sharpless, *Angew. Chem. Int'l. Ed.* 40 (11): 2004 (2001)). In some embodiments, the attachment component can include one functional group or a plurality of functional groups that result in a plurality of covalent bonds with the nanoparticle.

Table 1 provides an additional non-limiting, representative list of functional groups that can be used in the present invention.

TABLE 1

Exemplary Functional Group Pairs for Conjugation Chemistry

| Functional Groups: | Reacts with: |
|---|---|
| Ketone and aldehyde groups | Amino, hydrazido and aminooxy |
| Imide | Amino, hydrazido and aminooxy |
| Cyano | Hydroxy |

TABLE 1-continued

Exemplary Functional Group Pairs for Conjugation Chemistry

| Functional Groups: | Reacts with: |
|---|---|
| Alkylating agents (such as haloalkyl groups and maleimido derivatives) | Thiol, amino, hydrazido, aminooxy |
| Carboxyl groups (including activated carboxyl groups) | Amino, hydroxyl, hydrazido, aminooxy |
| Activated sulfonyl groups (such as sulfonyl chlorides) | Amino, hydroxyl, hydrazido, aminooxy |
| Sulfhydryl | Sulfhydryl, maleimido |
| His-tag (such as 6-His tagged peptide or protein) | Nickel nitriloacetic acid |

In other embodiments, an attachment component can be attached to a nanoparticle by non-covalent interactions that can include but are not limited to affinity interactions, metal coordination, physical adsorption, hydrophobic interactions, van der Waals interactions, hydrogen bonding interactions, magnetic interactions, electrostatic interactions, dipole-dipole interactions, antibody-binding interactions, hybridization interactions between complementary DNA, and the like. In some embodiments, an attachment component can be, e.g., a lipid or phospholipid, that incorporates into a nanoparticle. In certain embodiments, a lipid or phospholipid can be present in a lipid bilayer portion of a nanoparticle, wherein in certain embodiments the nanoparticle is a liposome. For example, an attachment component can be a lipid or phospholipid (e.g., a $C_8$-$C_{36}$ alkyl, which can be saturated or unsaturated) that interacts partially or wholly with the hydrophobic and/or hydrophilic regions of the lipid bilayer. In some embodiments, the attachment component can include one group that allows non-covalent interaction with the nanoparticle, but a plurality of groups is also contemplated. For example, a plurality of ionic charges can be used to produce sufficient non-covalent interaction between the attachment component and the nanoparticle. In alternative embodiments, the attachment component can include a plurality of lipids such that the plurality of lipids interacts with a bilayer membrane of a liposome or bilayer or monolayer coated on a nanoparticle. In certain embodiments, surrounding solution conditions can be modified to disrupt non-covalent interactions thereby detaching the attachment component from the nanoparticle.

As described further herein, some of the compounds of the present invention can include $R^1$, $R^2$, $R^3$, $R^4$, $R^5$ and/or $R^6$ as an attachment component. In some embodiments, the attachment component can include a phenyl group, cholesterol, or a lipid, such as a saturated or unsaturated $C_{10}$-$C_{24}$ alkyl group or a substituted saturated or unsaturated $C_{10}$-$C_{24}$ alkyl group. In certain exemplary embodiments, the attachment component can be selected to facilitate association of the attachment component with a lipid bilayer. For example, the length, sites and geometries of double bonds and/or substitutions of the alkyl groups can be selected to provide a desired level of incorporation with the lipid bilayer to allow modification of the surface properties of a liposome by display of other components, such as, e.g., targeting agents and/or stealth agents.

In some embodiments, the phosphonate conjugates can be directly attached to a nanoparticle by way of a linking group, $L^1$, $L^2$, $L^3$, $L^4$, $L^5$ and/or $L^6$. In these embodiments, $R^1$, $R^3$, $R^4$, and/or $R^6$ can be a nanoparticle. In other embodiments, $R^1$ is an attachment component, and the attachment component is a phospholipid. In some of the embodiments where $R^1$ is a phospholipid, the phospholipid has the formula:

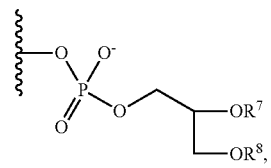

wherein each of $R^7$ and $R^8$ is independently selected from a saturated or unsaturated $C_{10-24}$ alkyl or alkanoyl group and a substituted saturated or unsaturated $C_{10}$-$C_{24}$ alkyl or alkanoyl group. In certain embodiments, each of $R^7$ and $R^8$ is independently selected from saturated or unsaturated $C_{10}$-$C_{18}$ alkyl or alkanoyl group and a substituted saturated or unsaturated $C_{10}$-$C_{18}$ alkyl or alkanoyl group. Suitable alkanoyl groups include, but are not limited to, decanoyl, undecanoyl, lauroyl, tridecanoyl, myristoyl, pentadecanoyl, palmitoyl, heptadecanoyl, stearoyl, nonadecanoyl, arachidoyl, and the like. Other phospholipids generally known in the art and described herein can also be used.

In some embodiments, the phosphonate conjugates can be prepared to modify the surface characteristics (e.g., hydrophilic or hydrophobic characteristics) of a nanoparticle. For example, positively and negatively charged groups can be included in the conjugates and further incorporated with a nanoparticle. In certain embodiments, acidic groups can be included in the conjugate to incorporate a negative charge on the surface of a liposome. As provided herein, the conjugates of the present invention can include a $[L^2-R^2]_n$ group that can be used to modify the surface characteristics. n can be an integer of 0, 1 or 2. In some embodiments, $L^2$ can be a bond or a linking group. $R^2$ can include, but is not limited to, a stealth agent, $C_1$-$C_{10}$ alkyl, a carboxylic acid or ester, a phosphonic acid or ester, a sulfonic acid or ester, or a hydroxy.

Linking Groups

Linking groups are another feature of the phosphonate conjugates of the present invention. One of ordinary skill in the art can appreciate that a variety of linking groups are known in the art and can be found, for example, in the following reference: Hermanson, G. T., *Bioconjugate Techniques*, $2^{nd}$ Ed., Academic Press, Inc. (2008). Linking groups of the present invention can be used to provide additional properties to the compounds, such as providing spacing between different portions of the compounds. This spacing can be used, for example, to overcome steric hindrance issues caused by a nanoparticle, e.g., when a targeting agent spaced a distance away from the nanoparticle can bind to a target. In some embodiments, linking groups can be used to change the physical properties of the compounds.

In some embodiments, the phosphonate conjugates of the present invention include $L^1$, $L^2$, $L^3$, $L^4$, $L^5$ and $L^6$, which can each independently be a linking group or a bond. In certain embodiments, $L^1$, $L^2$, $L^3$, $L^4$, $L^5$ and $L^6$ can each independently be selected to be a hydrophilic, non-immunogenic water soluble linking group. The hydrophilic, non-immunogenic water soluble linking groups of the present invention can include, but are not limited to, polyethylene glycol, polypropylene glycol, polyvinyl alcohol, polycarboxylate, polysaccharide, and dextran. One of ordinary skill in the art will appreciate that the length and/or chemical properties of a linking group can be selected for certain applications, such as the spacing considerations discussed above.

In other embodiments, the linking groups can be, for example, $C_{1-30}$ alkylene linking groups or similar heteroalkylene linking groups (an alkylene linking group in which the carbon chain is interrupted by from one to ten heteroatoms selected from O, N and S). Alternatively, in some embodiments, the linking groups can include an aryl moiety such as a phenylene ring or a heteroaryl counterpart. In yet other embodiments, linking groups can include alkylene or heteroalkylene linking groups substituted with amido, amino, keto, and hydroxyl groups.

Stealth Agents

In some embodiments, the phosphonate conjugates can include at least one stealth agent. For example, in certain embodiments, $R^1$, $R^2$, $R^3$, $R^4$, $R^5$ and $R^6$ can be independently selected to be a stealth agent. A stealth agent can prevent nanoparticles from sticking to each other and to blood cells or vascular walls. In certain embodiments, stealth nanoparticles, e.g., stealth liposomes, can reduce immunogenicity and/or reactogenecity when the nanoparticles are administered to a subject. Stealth agents can also increase blood circulation time of a nanoparticle within a subject. In some embodiments, a nanoparticle can include a stealth agent such that, for example, the nanoparticle is partially or fully composed of a stealth agent or the nanoparticle is coated with a stealth agent. Stealth agents for use in the present invention can include those generally well known in the art. Suitable stealth agents can include but are not limited to dendrimers, polyalkylene oxide, polyethylene glycol, polyvinyl alcohol, polycarboxylate, polysaccharides, and/or hydroxyalkyl starch. Stealth agents can be attached to the phosphonate conjugates of the present invention through covalent and/or non-covalent attachment, as described above with respect to the attachment component.

In certain embodiments, a stealth agent can include a polyalkylene oxide, such as "polyethylene glycol," which is well known in the art and refers generally to an oligomer or polymer of ethylene oxide. Polyethylene glycol (PEG) can be linear or branched, wherein branched PEG molecules can have additional PEG molecules emanating from a central core and/or multiple PEG molecules can be grafted to the polymer backbone. As is understood in the art, polyethylene glycol can be produced in as a distribution of molecular weights, which can be used to identify the type of PEG. For example, $PEG_{500}$ is identified by a distribution of PEG molecules having an average molecular weight of ~500 g/mol, as measured by methods generally known in the art. Alternatively, PEG can be represented by the following formula: H—[O—$(CH_2)_2]_m$—OH, in which m is the number of monomers present in the polymer (e.g., m can range from 1 to 200). For example, for a distribution of $PEG_{100}$ can include PEG polymers in which m is equal to 2. In another instance, $PEG_{1000}$ can include PEG molecules in which m is equal to 23. Alternatively, $PEG_{5000}$ can include PEG molecules in which m is equal to 114.

In certain embodiments, PEG can include low or high molecular weight PEG, e.g., $PEG_{100}$, $PEG_{500}$, $PEG_{2000}$, $PEG_{3400}$, $PEG_{5000}$, $PEG_{10000}$, or $PEG_{20000}$. In some embodiments, PEG can range between $PEG_{100}$ to $PEG_{10000}$, or $PEG_{1000}$ to $PEG_{10000}$, or $PEG_{1000}$ to $PEG_{5000}$. In certain embodiments, the stealth agent can be $PEG_{500}$, $PEG_{1000}$, $PEG_{2000}$, or $PEG_{5000}$. In certain embodiments, PEG can be terminated with a methyl ether, an alcohol, or a carboxylic acid. In certain embodiments, the stealth agent can include at least two PEG molecules each linked together with a linking group. Linking groups can include those described above, e.g., amide linkages. In some embodiments, PEGylated-lipids are present in a bilayer of the nanoparticle, e.g., a liposome, in an amount sufficient to make the nanoparticle "stealth," wherein a stealth nanoparticle shows reduced immunogenicity.

Therapeutic Agents

In some embodiments, the compounds of the present invention can include a therapeutic agent, diagnostic agent, or a combination thereof. In certain embodiments, the therapeutic and/or diagnostic agent can be associated directly with a phosphonate conjugate of the present invention. For example, the therapeutic and/or diagnostic agent can be covalently attached to the phosphonate conjugate. In other embodiments, the therapeutic agent and/or diagnostic agent can be present anywhere in, on, or around a nanoparticle associated with the phosphonate conjugates of the present invention. In some embodiments, the therapeutic agent and/or diagnostic agent can be embedded in, encapsulated in, or tethered to the nanoparticle. In certain embodiments, the nanoparticle is a liposome and the diagnostic and/or therapeutic agent is encapsulated in the liposome.

A therapeutic agent used in the present invention can include any agent directed to treat a condition in a subject. In general, any therapeutic agent known in the art can be used, including without limitation agents listed in the United States Pharmacopeia (U.S.P.), Goodman and Gilman's *The Pharmacological Basis of Therapeutics*, 10th Ed., McGraw Hill, 2001; Katzung, Ed., *Basic and Clinical Pharmacology*, McGraw-Hill/Appleton & Lange, 8th ed., Sep. 21, 2000; *Physician's Desk Reference* (Thomson Publishing; and/or *The Merck Manual of Diagnosis and Therapy*, 18th ed., 2006, Beers and Berkow, Eds., Merck Publishing Group; or, in the case of animals, *The Merck Veterinary Manual*, 9th ed., Kahn Ed., Merck Publishing Group, 2005; all of which are incorporated herein by reference.

Therapeutic agents can be selected depending on the type of disease desired to be treated. For example, certain types of cancers or tumors, such as carcinoma, sarcoma, leukemia, lymphoma, myeloma, and central nervous system cancers as well as solid tumors and mixed tumors, can involve administration of the same or possibly different therapeutic agents. In certain embodiments, a therapeutic agent can be delivered to treat or affect a cancerous condition in a subject and can include chemotherapeutic agents, such as alkylating agents, antimetabolites, anthracyclines, alkaloids, topoisomerase inhibitors, and other anticancer agents. In some embodiments, the agents can include antisense agents, microRNA, siRNA and/or shRNA agents.

In some embodiments, a therapeutic agent can include an anticancer agent or cytotoxic agent including but not limited to avastin, doxorubicin, cisplatin, oxaliplatin, carboplatin, 5-fluorouracil, gemcitibine or taxanes, such as paclitaxel and docetaxel. Additional anti-cancer agents can include but are not limited to 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflomithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In some embodiments, the therapeutic agents can be part of a cocktail of agents that includes administering two or more therapeutic agents. For example, a liposome having both cisplatin and oxaliplatin can be administered. In addition, the therapeutic agents can be delivered before, after, or with immune stimulatory adjuvants, such as aluminum gel or salt adjuvants (e.g., aluminum phosphate or aluminum hydroxide), calcium phosphate, endotoxins, toll-like receptor adjuvants and the like.

Therapeutic agents of the present invention can also include radionuclides for use in therapeutic applications. For example, emitters of Auger electrons, such as $^{111}$In, can be combined with a chelate, such as diethylenetriaminepentaacetic acid (DTPA) or 1,4,7,10-tetraazacyclododecane-1,4,7,10-tetraacetic acid (DOTA), and included in a targeted delivery composition, such as a liposome, to be used for treatment. Other suitable radionuclide and/or radionuclide-chelate combinations can include but are not limited to beta radionuclides ($^{177}$Lu, $^{153}$Sm, $^{88/90}$Y) with DOTA, $^{64}$Cu-TETA, $^{188/186}$Re(CO)$_3$-IDA; $^{188/186}$Re(CO)triamines (cyclic or linear), $^{188/186}$Re(CO)$_3$-Enpy2, and $^{188/186}$Re(CO)$_3$-DTPA.

As described above, the therapeutic agents used in the present invention can be associated with the nanoparticle in a variety of ways, such as being embedded in, encapsulated in, or tethered to the nanoparticle. Loading of the therapeutic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006). In a group of embodiments, one or more therapeutic agents can be loaded into liposomes. Loading of liposomes can be carried out, for example, in an active or passive manner. For example, a therapeutic agent can be included during the self-assembly process of the liposomes in a solution, such that the therapeutic agent is encapsulated within the liposome. In certain embodiments, the therapeutic agent may also be embedded in the liposome bilayer or within multiple layers of multilamellar liposome. In alternative embodiments, the therapeutic agent can be actively loaded into liposomes. For example, the liposomes can be exposed to conditions, such as electroporation, in which the bilayer membrane is made permeable to a solution containing therapeutic agent thereby allowing for the therapeutic agent to enter into the internal volume of the liposomes.

Diagnostic Agents

A diagnostic agent used in the present invention can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). In certain embodiments, $R^1$, $R^2$, $R^3$, $R^4$, $R^5$ and $R^6$ can be independently selected to be a diagnostic agent. A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl] benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra (methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

A radioisotope can be incorporated into some of the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the liposomes can be radiolabeled, for example, by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes* 2nd Ed.: Oxford Univ. Press (2003); Elbayoumi, T. A. & Torchilin, V. P., Eur. *J. Nucl. Med. Mol. Imaging* 33:1196-(2006); Mougin-Degraef, M. et al., *Int'l J. Pharmaceutics* 344:110-117 (2007).

In other embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) are preferred. For topical visualization using an endoscopic method, any dyes absorbing in the visible range are suitable.

In some embodiments, the non-ionizing radiation employed in the process of the present invention can range in wavelength from about 350 nm to about 1200 nm. In one exemplary embodiment, the fluorescent agent can be excited by light having a wavelength in the blue range of the visible portion of the electromagnetic spectrum (from about 430 nm to about 500 nm) and emits at a wavelength in the green range of the visible portion of the electromagnetic spectrum (from about 520 nm to about 565 nm). For example, fluorescein dyes can be excited with light with a wavelength of about 488 nm and have an emission wavelength of about 520 nm. As another example, 3,6-diaminopyrazine-2,5-dicarboxylic acid can be excited with light having a wavelength of about 470 nm and fluoresces at a wavelength of about 532 nm. In another embodiment, the excitation and emission wavelengths of the optical agent may fall in the near-infrared range of the electromagnetic spectrum. For example, indocyanine dyes, such as indocyanine green, can be excited with light with a wavelength of about 780 nm and have an emission wavelength of about 830 nm.

In yet other embodiments, the diagnostic agents can include but are not limited to magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to Gadopentetic acid, Gadoteric acid, Gadodiamide, Gadolinium, Gadoteridol, Mangafodipir, Gadoversetamide, Ferric ammonium citrate, Gadobenic acid, Gadobutrol, or Gadoxetic acid. Superparamagnetic agents can include but are not limited to superparamagnetic iron oxide and Ferristene. In certain embodiments, the diagnostic agents can include x-ray contrast agents as provided, for example, in the following references: H. S Thomsen, R. N. Muller and R. F. Mattrey, Eds., *Trends in Contrast Media*, (Berlin: Springer-Verlag, 1999); P. Dawson, D. Cosgrove and R. Grainger, Eds., *Textbook of Contrast Media* (ISIS Medical Media 1999); Torchilin, V. P., *Curr. Pharm. Biotech.* 1:183-215 (2000); Bogdanov, A. A. et al., *Adv. Drug Del. Rev.* 37:279-293 (1999); Sachse, A. et al., *Investigative Radiology* 32(1):44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iobitridol, iodixanol, iotrolan and iosimenol.

Similar to therapeutic agents described above, the diagnostic agents can be associated with the nanoparticle in a variety of ways, including for example being embedded in, encapsulated in, or tethered to the nanoparticle. Similarly, loading of the diagnostic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006).

Targeting Agents

In some embodiments, the phosphonate conjugates of the present invention can also include at least one targeting agent. For example, in certain embodiments, $R^1$, $R^2$, $R^3$, $R^4$, $R^5$ and $R^6$ can be independently selected to be a targeting agent. Generally, the targeting agents of the present invention can associate with any target of interest, such as a target associated with an organ, tissues, cell, extracellular matrix, or intracellular region. In certain embodiments, a target can be associated with a particular disease state, such as a cancerous condition. Alternatively, a targeting agent can target one or more particular types of cells that can, for example, have a target that indicates a particular disease and/or particular state of a cell, tissue, and/or subject. In some embodiments, the targeting agent can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell. In certain embodiments, suitable targets can include mucins such as MUC-1 and MUC-4, growth factor receptors such as EGFR, Claudin 4, nucleolar phosphoproteins such as nucleolin, chemokine receptors such as CCR7, receptors such as somatostatin receptor 4, Erb-B2 (erythroblastic leukaemia oncogene homologue 2) receptor, CD44 receptor, and VEGF receptor-2 kinase.

In certain embodiments, a targeting agent can include a small molecule mimic of a target ligand (e.g., a peptide mimetic ligand), a target ligand (e.g., an RGD peptide containing peptide or folate amide), or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like.

The targeting agents of the present invention can also include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., *Trends in Biotech.* 26(8): 442-449 (2008)). In the present invention, suitable aptamers can be linear or cyclized and can include oligonucleotides having less than about 150 bases (i.e., less than about 150 mer). Aptamers can range in length from about 100 to about 150 bases or from about 80 to about 120 bases. In certain embodiments, the aptamers can range from about 12 to 40 about bases, from about 12 to about 25 bases, from about 18 to about 30 bases, or from about 15 to about 50 bases. The aptamers can be developed for use with a suitable target that is present or is expressed at the disease state, and includes, but is not limited to, the target sites noted herein.

IV. Methods of Preparing Phosphonate Conjugates and Associated Components

The phosphonate conjugates can be produced in a variety of ways. In one aspect, the present invention includes a method of preparing a phosphonate conjugate, the method comprising: combining a primary amine compound having the formula: $H_2N(L^1)\text{-}(R^1)$, a carbonyl compound having the formula: $O\text{=}C[(L^2)\text{-}(R^2)]_n$, and a H-phosphonate compound having the formula:

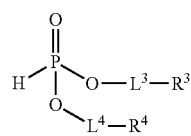

under conditions sufficient to form the phosphonate conjugate having the formula:

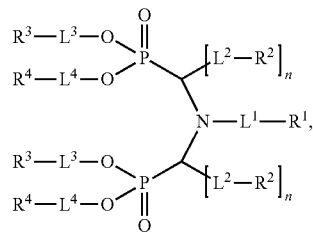

wherein each $L^1$, $L^2$, $L^3$ and $L^4$ is independently selected from the group consisting of a bond and a linking group; $R^1$ is selected from the group consisting of a nanoparticle, an attachment component, a targeting agent, a diagnostic agent, a stealth agent, and a tetrapodal presentation component; each $R^2$ is independently selected from the group consisting of a stealth agent, $C_1\text{-}C_{10}$ alkyl, a carboxylic acid or ester, a phosphonic acid or ester, a sulfonic acid or ester, and a hydroxy; each $R^3$ and $R^4$ is independently selected from the group consisting of H, an attachment component, a targeting agent, a diagnostic agent, and a stealth agent, wherein at least one of $R^3$ or $R^4$ is other than H; and n is an integer from 0 to 2, wherein when n is 0 or 1 the carbonyl compound is an aldehyde.

In another aspect, the present invention includes a method of preparing a phosphonate conjugate. The method includes combining a secondary amine compound having the formula: $HN[(L^1)\text{-}(R^1)](R^9)$, a carbonyl compound having the formula: $O\text{=}C[(L^2)\text{-}(R^2)]_n$, and a H-phosphonate compound having the formula:

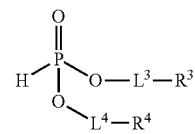

under conditions sufficient to form the phosphonate conjugate having the formula:

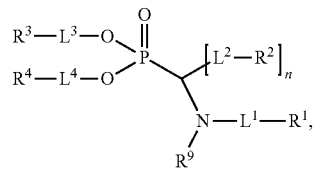

wherein each $L^1$, $L^2$, $L^3$ and $L^4$ is independently selected from the group consisting of a bond and a linking group; $R^1$ is selected from the group consisting of a nanoparticle, an attachment component, a targeting agent, a diagnostic agent and a stealth agent; $R^2$ is independently selected from the group consisting of a stealth agent, $C_1\text{-}C_{10}$ alkyl, a carboxylic acid or ester, a phosphonic acid or ester, a sulfonic acid or ester, and a hydroxy; each $R^3$ and $R^4$ is independently selected from the group consisting of H, an attachment component, a targeting agent, a diagnostic agent, and a stealth agent, wherein at least one of $R^3$ or $R^4$ is other than H; $R^9$ is selected from the group consisting of a $C_1\text{-}C_{10}$ alkyl group; and n is an integer from 0 to 2, wherein when n is 0 the carbonyl compound is formaldehyde.

In general, the reactions used to make the phosphonate conjugates include a H-phosphonate compound, a carbonyl compound, and a primary amine compound or a secondary amine compound. These compounds can be combined in any order during synthesis to reach the final phosphonate conjugates. For example, in some embodiments, the primary amine compound or secondary amine compound and the carbonyl compound can be combined to form an intermediate compound before being combined with a H-phosphonate compound to form the final phosphonate conjugate. In other embodiments, a H-phosphonate compound can be combined with a carbonyl compound to form an intermediate compound before being combined with a primary amine compound or secondary amine compound to form the final phosphonate conjugate. In certain embodiments, the necessary compounds can be combined together in one reaction to produce the final phosphonate conjugates. For certain conjugates, the ratio of a H-phosphonate compound, a carbonyl compound, and a primary amine compound can be 2:2:1. For other conjugates, the ratio of a H-phosphonate compound, a carbonyl compound, and a secondary amine compound can be 1:1:1. The ratio of the different compounds will depend on the particular reaction conditions and desired phosphonate conjugates.

Figure 2:
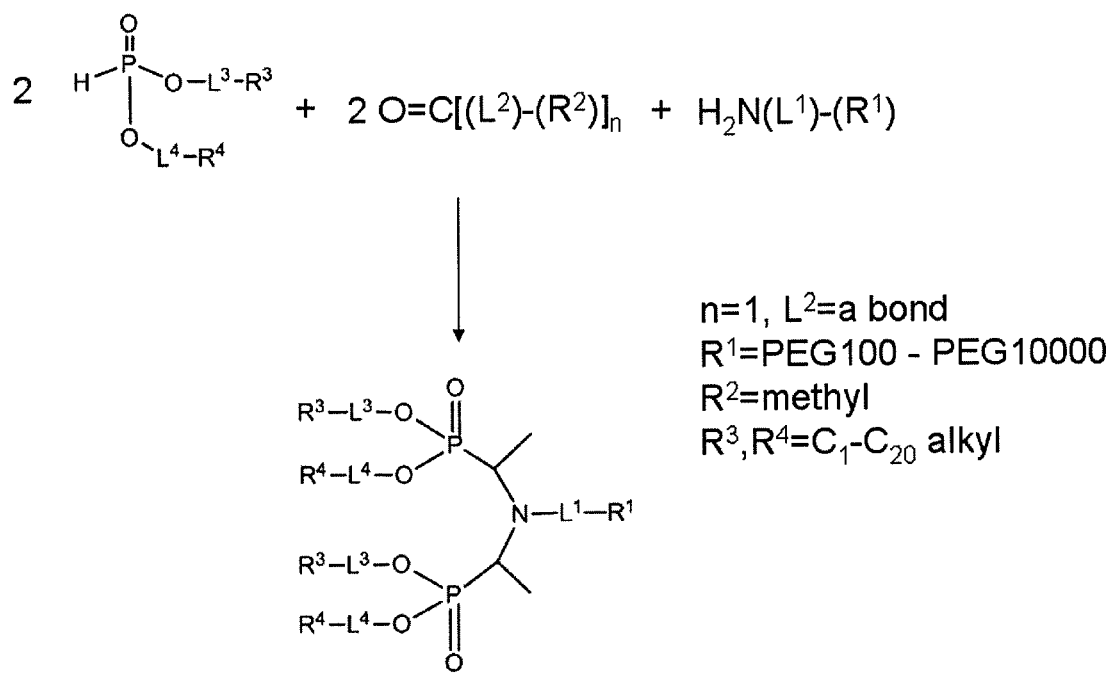
FIG. 2 depicts an example synthetic method for producing a phosphonate conjugate of the present invention.

As provided herein, the reactions involving a H-phosphonate compound, a primary or a secondary amine compound, and a carbonyl compound can be used to produce a large variety of compounds that can include an attachment component, a targeting agent, a diagnostic agent, a therapeutic agent, a stealth agent, or a combination thereof. As shown, for example in FIGS. 1 and 2, a H-phosphonate compound, a carbonyl compound, and a primary amine compound at ratios of 2:2:1 can be combined to form phosphonate conjugates of the present invention. As shown in FIG. 1, the phosphonate conjugate can include $R^1$ as a PEG group ranging from $PEG_{1000}$-$PEG_{10000}$. $R^3$ and $R^4$ can also be selected from $C_1$-$C_{20}$ alkyl groups to facilitate, for example, attachment to a bilayer membrane of a liposome. In this particular example, n is zero in which the carbonyl compound then is formaldehyde. Similarly, as shown in FIG. 2, the carbonyl compound can have n as 1 and $R^2$ as a methyl group, which changes the structure of the phosphonate conjugate in FIG. 1. One of ordinary skill in the art will appreciate the variety of possible combinations that can be used to produce the scope of phosphonate conjugates disclosed herein.

Figure 3:
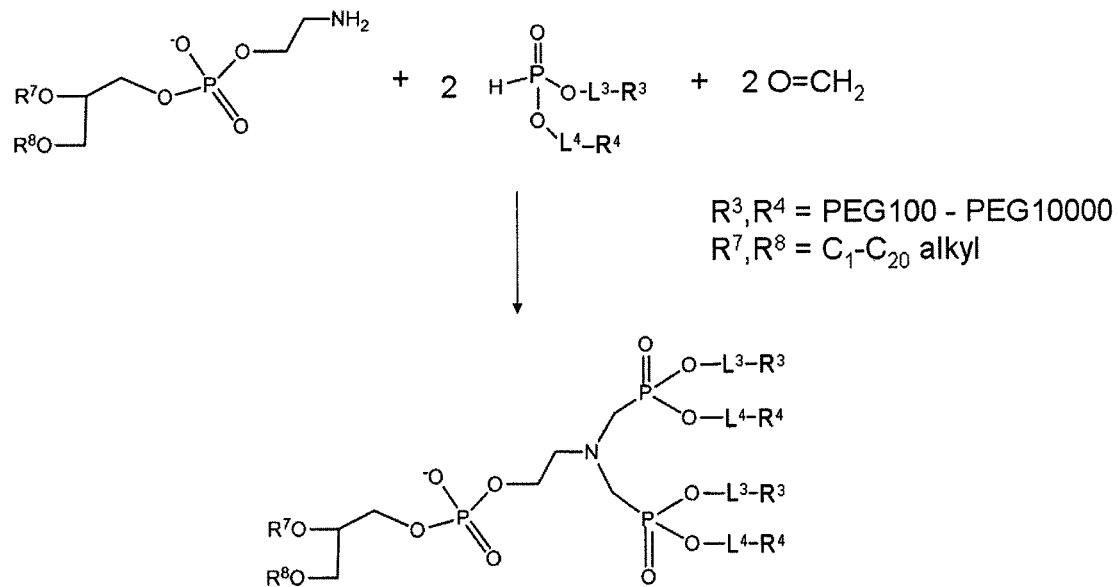
FIG. 3 depicts an example synthetic method for making a phosphonate conjugate of the present invention.

In some embodiments, phosphonate conjugates can be produced so as to provide a presentation assembly that can extend, e.g., from the surface of a nanoparticle. As shown in FIG. 3, a lipid molecule can include a primary amine and $R^7$ and $R^8$, which can be, e.g., $C_1$-$C_{20}$ alkyl groups. In this example, n is 0 and $L^3$ and $L^4$ can be a bond or a short alkylene group (e.g., $C_1$-$C_6$) or other linking group to allow for desired spacing or other characteristics desired for a particular application. As shown, the lipid molecule can be combined with a H-phosphonate compound and formaldehyde at a ratio of 1:2:2, respectively, to form a phosphonate conjugate presenting a tetrapodal assembly of $R^3$ and $R^4$.

Figure 4:
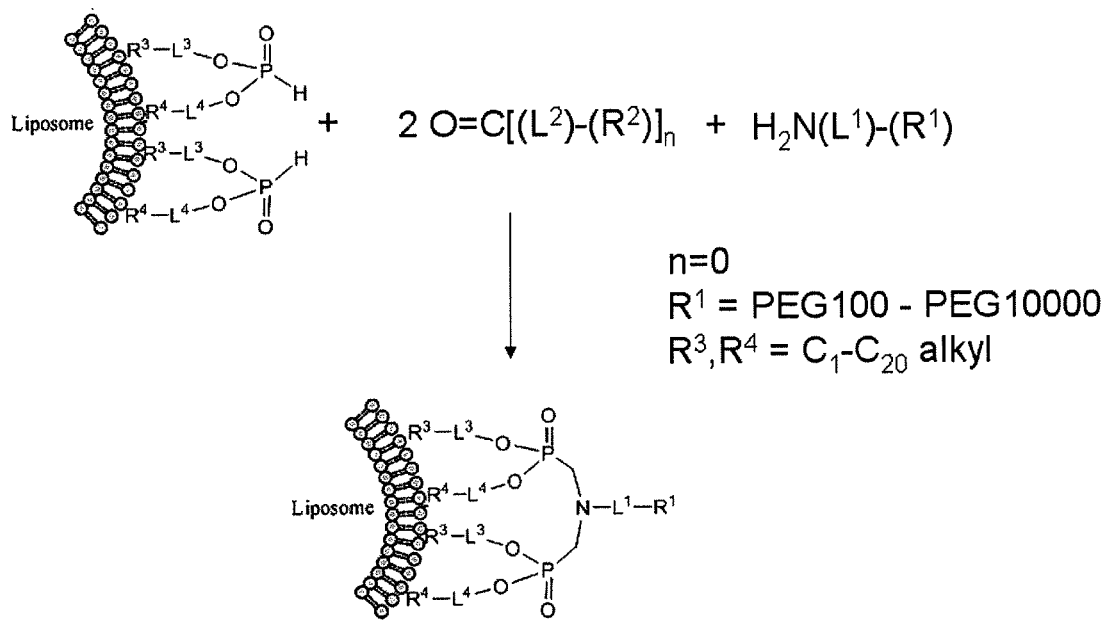
FIG. 4 depicts an example synthetic method for making a phosphonate conjugate of the present invention on the surface of a liposome.

In certain embodiments, the methods of making these compounds can be combined with nanoparticles to allow synthesis of the phosphonate conjugates while one of the starting materials, e.g., a H-phosphonate compound, is attached to the nanoparticle. As depicted in example FIG. 4, two adjacent H-phosphonate compounds in a lipid bilayer membrane can be combined with two equivalents of a carbonyl compound, $O=C[(L^2)-(R^2)]_n$, and one equivalent of a primary amine compound, $H_2N(L^1)-(R^1)$, to produce the phosphonate conjugates of the present invention on the surface of a nanoparticle. As shown, for example, in FIG. 4, $R^3$ and $R^4$ can be attachment components, e.g., a $C_1$-$C_{20}$ alkyl group, that is embedded in the lipid bilayer of a liposome. The prepared liposomes having the H-phosphonate compound can then be combined with the primary amine compound, which, e.g., includes a stealth agent, such as PEG ranging from $PEG_{100}$-$PEG_{10000}$. After a hydrophosphonylation reaction including the carbonyl compound, the stealth agent can be displayed on the surface of the liposome, thereby transforming the liposome to a stealth liposome.

Figure 5:
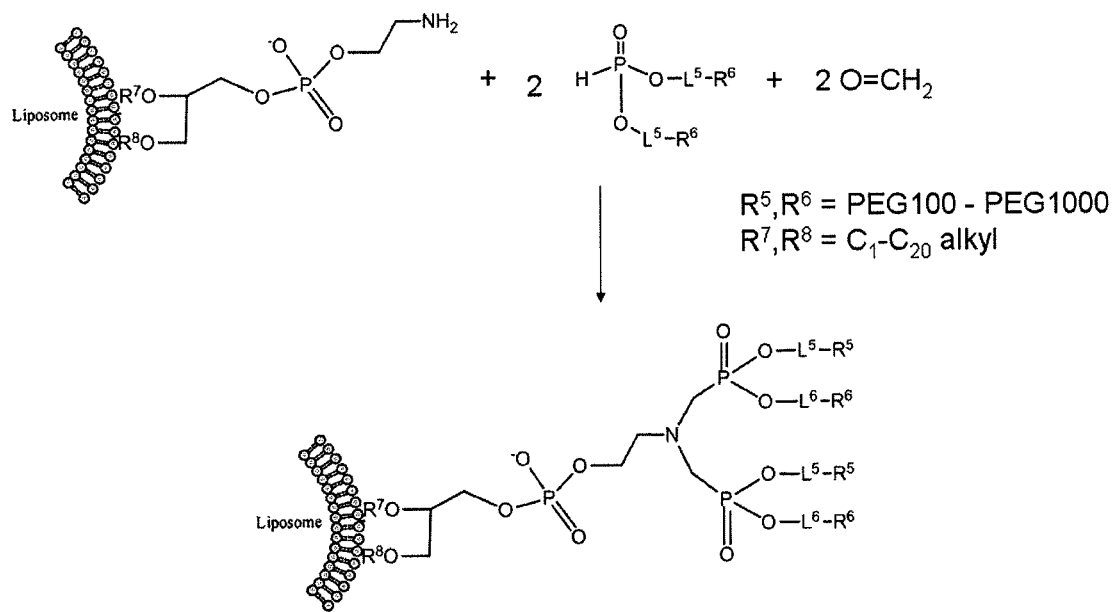
FIG. 5 depicts an example synthetic method for making a phosphonate conjugate of the present invention on the surface of a liposome.

As depicted in FIG. 5, a similar strategy can be used to produce a presentation assembly that extends from the surface of the nanoparticle. A lipid molecule can include a primary amine that extends from the surface, and $R^7$ and $R^8$ can be, e.g., $C_1$-$C_{20}$ alkyl groups that embed in the lipid bilayer. When combined with two equivalents of a H-phosphonate compound and formaldehyde, a hydrophosphonylation reaction can form a bridge between the two H-phosphonate compounds and also present $R^5$ and $R^6$ on the surface of the liposome, in which $R^5$ and $R^6$ can be a stealth agent, such as PEG ranging from $PEG_{100}$-$PEG_{10000}$. As described in more detail above, the linking groups $L^1$, $L^2$, and $L^3$ can be independently selected as a linking group or a bond to allow for desired spacing or other characteristics desired for a particular application. One of ordinary skill in the art will appreciate the variety of synthetic methods that can be used to produce the phosphonate conjugates of the present invention on the surface of a nanoparticle.

As will be appreciated by one of ordinary skill in the art, the starting materials and the intermediates of the synthetic reaction schemes described herein can be isolated and purified if desired using conventional techniques, including but not limited to, filtration, distillation, crystallization, chromatography, and the like. Such materials can be characterized using conventional means, including physical constants and spectral data. Unless specified to the contrary, the reactions described herein can be conducted under an inert atmosphere at atmospheric pressure at a reaction temperature range of from about −78° C. to about 150° C., or from about 0° C. to about 125° C., and in some embodiments at about room (or ambient) temperature, e.g., about 20° C. The reactions described herein can be carried out in a variety of solvents that can depend on the particular reaction being used to produce an intermediate or final product described herein. In some embodiments, the reaction solvents can include an organic solvents, such as an aprotic solvent (e.g., THF or ether). In certain embodiments, the reaction solvents can be aqueous solvents and can include additional buffers, salts, additives, and the like. Certain reactions described herein can include reflux conditions to, for example, purify certain compounds described herein.

While the hydrophosphonylation reactions provide several advantages for producing the phosphonate conjugates of the present invention on a nanoparticle, other methods can be used to make the compounds. For example, the H-phosphonate compounds, primary and secondary amine compounds, and carbonyl compounds can be reacted together to form the phosphonate conjugates of the present invention. Subsequently, the phosphonate conjugates can be attached to a nanoparticle. In some embodiments, the phosphonate conjugates can be incorporated into liposomes by first producing the liposomes using standard methods, e.g., extrusion, and subsequently attaching the phosphonate conjugates to the liposomes. In other embodiments, the phosphonate conjugates can be incorporated into the liposome bilayer during formation of the liposomes by, e.g., drying the phosphonate conjugates and lipid components together and then resuspending the mixture in aqueous solution to form the liposomes with the phosphonate conjugates associated with the bilayer.

It is also contemplated that the phosphonate conjugates can be produced using other synthetic sequences. For example, a primary amine compound including $R^1$ and $L^1$, as shown in FIG. 1, can be reacted with a H-phosphonate that does not contain $R^3$ and $R^4$. In such embodiments, $L^3$ and $L^4$ can be linking groups that include a functional group for bonding to an $R^3$ and/or $R^4$, which can include, e.g., a targeting agent, a stealth agent, or a diagnostic agent. Accordingly, $R^3$ and/or $R^4$ can be reacted with the functional group of $L^3$ and $L^4$ to produce a final phosphonate conjugate. One of ordinary skill in the art will appreciate that there are several other possible synthetic orders to produce the phosphonate conjugates of the present invention. For example, $R^3$ and $R^4$ can be the same and thus, for example, if $R^3$ and $R^4$ are each a targeting agent, then $L^3$ and $L^4$ can each contain functional groups that can react with the targeting agent to produce a phosphonate conjugate of the present invention.

Nanoparticles

As provided herein, the present invention includes the use of nanoparticles that can be produced by a variety of ways generally known in the art and methods of making such nanoparticles can depend on the particular nanoparticle desired. Any measuring technique available in the art can be used to determine properties of the targeted delivery compositions and nanoparticles. For example, techniques such as dynamic light scattering, x-ray photoelectron microscopy, powder x-ray diffraction, scanning electron microscopy (SEM), transmission electron microscopy (TEM), and atomic force microscopy (AFM) can be used to determine average size and dispersity of the nanoparticles and/or targeted delivery compositions.

Liposomes used in the present invention can be made using a variety of techniques generally well known in the art. (See, e.g., Williams, A. P., Liposomes: A Practical Approach, $2^{nd}$ Edition, Oxford Univ. Press (2003); Lasic, D. D., Liposomes in Gene Delivery, CRC Press LLC (1997)). For example, liposomes can be produced by but are not limited to techniques such as extrusion, agitation, sonication, reverse phase evaporation, self-assembly in aqueous solution, electrode-based formation techniques, microfluidic directed formation techniques, and the like. In certain embodiments, methods can be used to produce liposomes that are multilamellar and/or unilamellar, which can include large unilamellar vesicles (LUV) and/or small unilamellar vesicles (SUV). Similar to self-assembly of liposomes in solution, micelles can be produced using techniques generally well known in the art, such that amphiphilic molecules will form micelles when dissolved in solution conditions sufficient to form micelles. Lipid-coated bubbles and lipoproteins can also be constructed using methods known in the art (See, e.g., Farook, U., *J. R. Soc. Interface*, 6(32): 271-277 (2009); Lacko et al., *Lipoprotein Nanoparticles as Delivery Vehicles for Anti-Cancer Agents* in Nanotechnology for Cancer Therapy, CRC Press (2007)).

Methods of making polymeric nanoparticles that can be used in the present invention are generally well known in the art (See, e.g., Sigmund, W. et al., Eds., Particulate Systems in Nano- and Biotechnologies, CRC Press LLC (2009); Karnik et al., *Nano Lett.*, 8(9): 2906-2912 (2008)). For example, block copolymers can be made using synthetic methods known in the art such that the block copolymers can self-assemble in a solution to form polymersomes and/or block copolymer micelles. Niosomes are known in the art and can be made using a variety of techniques and compositions (Baillie A. J. et al., *J. Pharm. Pharmacol.*, 38:502-505 (1988)). Magnetic and/or metallic particles can be constructed using any method known in the art, such as co-precipitation, thermal decomposition, and microemulsion. (See also Nagarajan, R. & Hatton, T. A., Eds., Nanoparticles Synthesis, Stabilization, Passivation, and Functionalization, Oxford Univ. Press (2008)). Gold particles and their derivatives can be made using a variety of techniques generally known in the art, such as the Turkevich method, Brust method, Perraut Method or sonolysis (See also, Grzelczak et al., Chem. Soc. Rev., 37: 1783-1791 (2008)). In some embodiments, the attachment component can be attached through sulfur-gold tethering chemistry. Quantum dots or semiconductor nanocrystals can be synthesized using any method known in the art, such as colloidal synthesis techniques. Generally, quantum dots can be composed of a variety of materials, such as semiconductor materials including cadmium selenide, cadmium sulfide, indium arsenide, indium phosphide, and the like.

Other Associated Components

As described herein, the phosphonate conjugates of the present invention can include components, such as targeting agents, stealth agents, diagnostic agents, therapeutic agents, and attachment components. One of ordinary skill will appreciate the standard, generally well known techniques that can be used to produce the various combinations of components included in the phosphonate conjugates. For example, targeting agents, stealth agents, diagnostic agents, therapeutic agents can be attached to the phosphonate conjugates of the present invention through covalent and/or non-covalent attachment, as described above with respect to the attachment component.

With respect to targeting agents, for certain embodiments the targeting agent can include an aptamer. Aptamers for a particular target can be indentified using techniques known in the art, such as but not limited to, in vitro selection processes, such as SELEX™ (systematic evolution of ligands by exponential enrichment), or MonoLex™ technology (single round aptamer isolation procedure for AptaRes AG), in vivo selection processes, or combinations thereof. (See e.g., Ellington, A. D. & Szostak, J. W., *Nature* 346(6287): 818-22; Bock et al., *Nature* 355(6360): 564-6 (1992)). In some embodiments, the above mentioned methods can be used to identify particular DNA or RNA sequences that can be used to bind a particular target site of interest, as disclosed herein. Once a sequence of a particular aptamer has been identified, the aptamer can be constructed in a variety of ways known in the art, such as phosphoramidite synthesis. For peptide aptamers, a variety of identification and manufacturing techniques can be used (See e.g., Colas, P., *J. Biol.* 7:2 (2008); Woodman, R. et al., *J. Mol. Biol.* 352(5): 1118-33 (2005).

Aptamers can be attached to the H-phosphonate compounds, primary and secondary amine compounds, and the carbonyl compounds by a variety of ways. For example, linking groups on the H-phosphonate compounds and/or primary or secondary amine compounds can be reacted with a 3' or 5' end of the aptamer. In alternative embodiments, the aptamer can be synthesized sequentially by adding one nucleic acid at a time to a linking group on the H-phosphonate compounds and primary or secondary amine compounds. One of ordinary skill in the art will appreciate the well known techniques that can be used to include aptamers in the phosphonate conjugates of the present invention.

V. Methods of Administering Targeted Delivery Compositions

The present invention also includes targeted delivery compositions that include a phosphonate conjugate. In one aspect, the present invention includes a targeted delivery composition comprising a phosphonate conjugate described herein, wherein each of $R^3$ and $R^4$ is an attachment component attached to a nanoparticle, and $R^1$ is selected from a targeting agent, a diagnostic agent and a stealth agent. As described in more detail above, the attachment component can attach to a nanoparticle in several ways, for example, the attachment component can be a lipid that associates with a bilayer of a liposome. In certain embodiments, the targeted delivery composition can include a liposome and each of $R^3$ and $R^4$ can be associated with a bilayer of the liposome and can independently be a lipid or cholesterol. In other embodiments, $R^1$ of the phosphonate conjugates can be a nanoparticle or an attachment component attached to a nanoparticle and each of $R^3$ and $R^4$ can be a targeting agent, a diagnostic agent or a stealth agent.

The targeted delivery compositions and methods of the present invention can be used for treating and/or diagnosing any disease, disorder, and/or condition associated with a subject. In one embodiment, the methods of the present invention include a method for treating or diagnosing a cancerous condition in a subject, comprising administering to the subject a targeted delivery composition including a phosphonate conjugate of the present invention attached to a nanoparticle, wherein the composition also includes a therapeutic or diagnostic agent that is sufficient to treat or diagnose the condition and at least one of $R^1$, $R^3$ and $R^4$ is a targeting agent. In certain embodiments, the cancerous condition can include cancers that sufficiently express (e.g., on the cell surface or in the vasculature) a receptor that is being targeted by a targeting agent of a targeted delivery composition of the present invention.

In another embodiment, the methods of the present invention include a method of determining the suitability of a subject for a targeted therapeutic treatment, comprising administering to the subject a targeted delivery composition that includes a nanoparticle and a phosphonate conjugate described herein, wherein the phosphonate conjugate or nanoparticle comprises a diagnostic agent, and imaging the subject to detect the diagnostic agent, and at least one of $R^1$, $R^3$ and $R^4$ is a targeting agent.

Administration

In some embodiments, the present invention can include a targeted delivery composition and a physiologically (i.e., pharmaceutically) acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington: The Science and Practice of Pharmacy, 21st edition, 2005).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized targeted delivery compositions.

The targeted delivery composition of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which includes an effective amount of a packaged targeted delivery composition with a suppository base. Suitable suppository bases include natural or synthetic triglycerides or paraffin hydrocarbons. In addition, it is also possible to use gelatin rectal capsules which contain a combination of the targeted delivery composition of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of targeted delivery compositions can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a targeted delivery composition. The unit dosage form can be a packaged preparation, the package containing discrete quantities of preparation. The composition can, if desired, also contain other compatible therapeutic agents.

In therapeutic use for the treatment of cancer, the targeted delivery compositions including a therapeutic and/or diagnostic agent utilized in the pharmaceutical compositions of the present invention can be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the targeted delivery composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular targeted delivery composition in a particular patient. Determination of the proper dosage for a particular situation is within the skill of the practitioner. Generally, treatment is initiated with smaller dosages which are less than the optimum dose of the targeted delivery composition. Thereafter, the dosage is increased by small increments until the optimum effect under circumstances is reached. For convenience, the total daily dosage may be divided and administered in portions during the day, if desired.

In some embodiments, the targeted delivery compositions of the present invention may be used to diagnose a disease, disorder, and/or condition. In some embodiments, the targeted delivery compositions can be used to diagnose a cancerous condition in a subject, such as lung cancer, breast cancer, pancreatic cancer, prostate cancer, cervical cancer, ovarian cancer, colon cancer, liver cancer, esophageal cancer, and the like. In some embodiments, methods of diagnosing a disease state may involve the use of the targeted delivery compositions to physically detect and/or locate a tumor within the body of a subject. For example, tumors can be related to cancers that sufficiently express (e.g., on the cell surface or in the vasculature) a receptor that is being targeted by a targeting agent of a targeted delivery composition of the present invention. In some embodiments, the targeted delivery compositions can also be used to diagnose diseases other than cancer, such as proliferative diseases, cardiovascular diseases, gastrointestinal diseases, genitourinary disease, neurological diseases, musculoskeletal diseases, hematological diseases, inflammatory diseases, autoimmune diseases, rheumatoid arthritis and the like.

As disclosed herein, the targeted delivery compositions of the invention can include a diagnostic agent that has intrinsically detectable properties. In detecting the diagnostic agent in a subject, the targeted delivery compositions, or a population of particles with a portion being targeted delivery compositions, can be administered to a subject. The subject can then be imaged using a technique for imaging the diagnostic agent, such as single photon emission computed tomography (SPECT), magnetic resonance imaging (MRI), optical imaging, positron emission tomography (PET), computed tomography (CT), x-ray imaging, gamma ray imaging, and the like. Any of the imaging techniques described herein may be used in combination with other imaging techniques. In some embodiments, the incorporation of a radioisotope for imaging in a particle allows in vivo tracking of the targeted delivery compositions in a subject. For example, the biodistribution and/or elimination of the targeted delivery compositions can be measured and optionally be used to alter the treatment of patient. For example, more or less of the targeted delivery compositions may be needed to optimize treatment and/or diagnosis of the patient.

Targeted Delivery

In certain embodiments, the targeted delivery compositions of the present invention can be delivered to a subject to release a therapeutic or diagnostic agent in a targeted manner. For example, a targeted delivery composition can be delivered to a target in a subject and then a therapeutic agent embedded in, encapsulated in, or tethered to the targeted delivery composition, such as to the nanoparticle, can be delivered based on solution conditions in vicinity of the target. Solution conditions, such as pH, salt concentration, and the like, may trigger release over a short or long period of time of the therapeutic agent to the area in the vicinity of the target. Alternatively, an enzyme can cleave the therapeutic or diagnostic agent from the targeted delivery composition to initiate release. In some embodiments, the targeted delivery compositions can be delivered to the internal regions of a cell by endocytosis and possibly later degraded in an internal compartment of the cell, such as a lysosome. One of ordinary skill will appreciate that targeted delivery of a therapeutic or diagnostic agent can be carried out using a variety of methods generally known in the art.

Kits

The present invention also provides kits for administering the targeted delivery compositions to a subject for treating and/or diagnosing a disease state. Such kits typically include two or more components necessary for treating and/or diagnosing the disease state, such as a cancerous condition. Components can include targeted delivery compositions of the present invention, reagents, containers and/or equipment. In some embodiments, a container within a kit may contain a targeted delivery composition including a radiopharmaceutical that is radiolabeled before use. The kits can further include any of the reaction components or buffers necessary for administering the targeted delivery compositions. Moreover, the targeted delivery compositions can be in lyophilized form and then reconstituted prior to administration.

In certain embodiments, the kits of the present invention can include packaging assemblies that can include one or more components used for treating and/or diagnosing the disease state of a patient. For example, a packaging assembly may include a container that houses at least one of the targeted delivery compositions as described herein. A separate container may include other excipients or agents that can be mixed with the targeted delivery compositions prior to administration to a patient. In some embodiments, a physician may select and match certain components and/or packaging assemblies depending on the treatment or diagnosis needed for a particular patient.

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The following preparations and examples are given to enable those skilled in the art to more clearly understand and to practice the present invention. They should not be considered as limiting the scope of the invention, but merely as being illustrative and representative thereof.

VI. EXAMPLES

The starting materials and reagents used in preparing these compounds generally are either available from commercial suppliers, such as Aldrich Chemical Co., or are prepared by methods generally known to those skilled in the art following procedures set forth in the scientific and patent literature and references, such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Example 1

Preparation of Dialkyl Hydrogen Phosphonates

Figure 6:
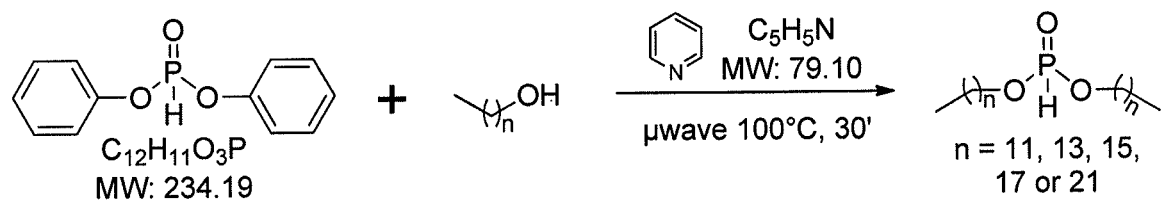
FIG. 6 shows a general reaction scheme to combine diphenyl phosphite with a 1-alkanol to form the dialkyl hydrogen phosphonates, in accordance with exemplary embodiments of the present invention.

A generalized synthetic procedure was used to produce dialkyl hydrogen phosphonates that could be further reacted to form some of the compounds of the present invention. As depicted in FIG. 6, the general reaction scheme was to combine diphenyl phosphite with a 1-alkanol to form the dialkyl hydrogen phosphonates. The following dialkyl hydrogen phosphonates were prepared as follows:

| n | 1-alkanol | 1-alkanol MW | Dialkyl phosphonate | Product MW |
|---|---|---|---|---|
| 11 | $C_{12}H_{26}O$ | 1-dodecanol 186.33 | $C_{24}H_{51}O_3P$ | 418.63 |
| 13 | $C_{14}H_{30}O$ | 1-tetradecanol 214.39 | $C_{28}H_{59}O_3P$ | 474.74 |
| 15 | $C_{16}H_{34}O$ | 1-hexadecanol 242.44 | $C_{32}H_{67}O_3P$ | 530.85 |
| 17 | $C_{18}H_{38}O$ | 1-octadecanol 270.49 | $C_{36}H_{75}O_3P$ | 586.95 |
| 21 | $C_{22}H_{46}O$ | 1-docosanol 326.60 | $C_{44}H_{91}O_3P$ | 699.17 |

In a 2-5 mL microwave vial, 3-6 mmol of diphenyl phosphite and 2.1 equivalents of the 1-alkanol were added. 2 equivalents (by volume) of anhydrous pyridine were syringed into vial, and the vial was sealed by crimping the top. The reaction mixture was exposed to microwave radiation using a Biotage™ Initiator Reactor at 100° C. for 30 minutes. The reaction mixture in $CDCl_3$ was checked for completion by $^{31}P$ NMR.

The reaction mixture was transferred into 100 mL round bottom flask and rotary evaporated at 70° C. to remove solvents. The crude product residue was purified by normal phase silica gel flash chromatography using hexanes/ethyl acetate gradient ($C_{12}$ product) or precipitation in acetone ($C_{14}$ through $C_{22}$ products). In each case, MS and NMR data was consistent with desired product.

Example 2

Preparation of Dioctadecyl Hydrogen Phosphonate

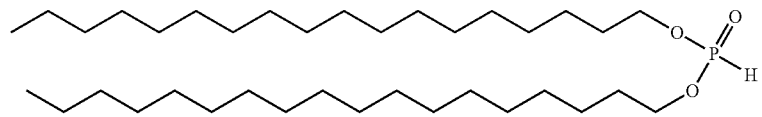 [SMILES: CCCCCCCCCCCCCCCCCCO[PH](=O)OCCCCCCCCCCCCCCCCCC]

To a 125 mL round-bottom flask (RBF) equipped with mechanical stirrer and thermocouple were added 1-octadecanol (25.41 g, 0.0939 mole, 2.2 eq.), diphenyl phosphite (10.0 g, 0.0427 mole, 1.0 eq.), and pyridine (4.053 g, 0.5124 mole, 1.2 eq) and the mixture was heated to 75° C. After 2.5 h, the completion of the reaction was checked by $^{31}$P NMR (CDCl$_3$): product at 7.8 ppm, intermediate mono-octadecyl phenyl phosphonate at 4.2 ppm, diphenyl phosphate at 0.35 ppm. The reaction showed ca. 94% (by integration) product, 1.5% intermediate, and 4.6% of a peak at 5.5 ppm. The mixture was cooled to 40-50° C., and ca. 50 mL dichloromethane was slowly added to prevent the material from solidifying and seizing the stirrer. The mixture was further diluted with 150 mL dichloromethane and transferred to a separatory funnel. The mixture was washed with 50 mL water, extracted with 3×75 mL 3N hydrochloric acid, and further washed with 75 mL each of water and brine. The organic layer was dried over anhydrous Na$_2$SO$_4$ and concentrated on the rotary evaporator (rotovap) to give a clear liquid that slowly solidifies upon standing.

To a clean 250 mL RBF equipped with mechanical stirrer was added 100 mL acetone. The concentrated product was added to the stirred acetone at ambient temperature via plastic pipette; the liquid precipitated to a fluffy white solid. The mixture was stirred for 1 h before filtering over Whatman™ #4 filter paper covered by a layer of Sharkskin™ paper to give a fluffy white wet cake. The wet cake was dried under vacuum overnight at ambient temperature. Yield: 19.11 g (76.3%). HRMS: [M+H]$^+$ calculated 587.5525, observed 587.5525; [M+Na]$^+$ calculated 609.5346, observed 609.5339. HLPC-MS: 587.25 [M+H]$^+$, 604.17 [M+NH$_4$]$^+$, 609.58 [M+Na]$^+$, $^{31}$P NMR (500 MHz, CDCl$_3$)=7.734 ppm. $^1$H and $^{13}$C NMR were consistent with desired structure.

Alternatively, after the initial reaction was deemed complete the crude reaction mixture in a 250 mL distillation flask was placed in a Kugelrohr distillation apparatus and the volatiles removed by placing the flask under high vacuum and gradually warming the Kugelrohr oven in 10° C. increments from 60° C. to 120° C. over approximately a 1.5 hour period and holding at 120° C. for 3 hours. The distillate receiver was cooled in a dry ice/acetone bath. After completing the distillation, the hot, liquefied product in the 250 mL distillation flask was poured into a tarred 125 mL glass storage jar, in which it solidified upon cooling. This afforded the product as a white waxy solid. An aliquot of this solid was examined by $^{31}$P NMR spectroscopy as a solution in CDCl$_3$, which exhibited a single peak at approximately δ 7.72. The only observable impurity by $^1$H and $^{13}$C NMR in the product is starting 1-octadecanol, which accounted for approximately 15 mol % of the isolated product.

Example 3

Preparation of Diolelyl Hydrogen Phosphonate

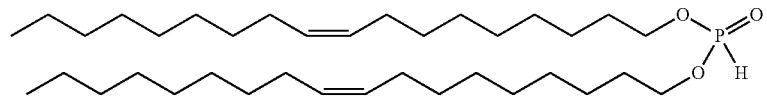 [SMILES: CCCCCCCC/C=C\CCCCCCCCO[PH](=O)OCCCCCCCC/C=C\CCCCCCCC]

To a 125 mL RBF equipped with mechanical stirrer and thermocouple were added olelyl alcohol (30.85 g, 0.115 mol, 2.2 eq.), diphenyl phosphite (12.23 g, 0.0522 mol, 1 eq.), and pyridine (4.96 g, 0.0627 mol, 1.2 eq.). The mixture was heated to 65° C. for 3 h. Completion of reaction was checked by $^{31}$P NMR (CDCl$_3$, 7.76 ppm). The mixture was cooled to <50° C., and 50 mL of dichloromethane was added. The mixture was further diluted with 150 mL of dichloromethane and transferred to a separatory funnel. The mixture was washed with 50 mL water, extracted with 3×75 mL 3N hydrochloric acid, and further washed with 75 mL each of water and brine. The organic layer was dried over anhydrous Na$_2$SO$_4$ and concentrated to give a colorless oil. The neat oil was transferred to a 250 mL separatory funnel and washed with 6×50 mL of acetonitrile (ACN). Yield: 19.86 g (65.2%). High Resolution Mass Spectrometry (HRMS): [M+Na]$^+$ calculated 605.5033, observed 605.5015: $^{31}$P NMR (500 MHz, CDCl$_3$)=7.734 ppm. $^1$H and $^{13}$C NMR are consistent with desired structure.

Example 4

Preparation of Dicholesteryl Hydrogen Phosphonate

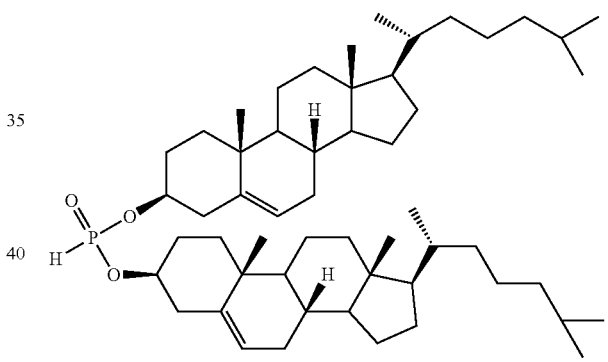

To a 250 mL RBF equipped with mechanical stirrer and thermocouple were added cholesterol (44.42 g, 0.1149 mol), diphenyl phosphite (12.23, 0.0522 mol), and pyridine (4.957, 0.0627 mol). The mixture was heated to 85-90° C., at which point it went from a solid to a stirable, fluid mass. After heating overnight, the completion of reaction was checked by $^{31}$P NMR (CDCl$_3$) with the major peak at 4.31 ppm, which was verified by HRMS to be the desired product. The mixture was cooled to <50° C. and 100 mL of chloroform was added to dissolve the solids. The mixture was further diluted with 150 mL of chloroform and transferred to a separatory funnel. The mixture was washed with 50 mL water, extracted with 3×50 mL 3N hydrochloric acid, and further washed with 50 mL each of water and brine. The organic layer was dried over anhydrous Na$_2$SO$_4$ and concentrated on the rotovap to give a viscous orange oil (this slowly solidifies upon standing).

To a clean 500 mL RBF equipped with mechanical stirrer was added 200 mL acetone. The concentrated product was added to the stirred acetone at ambient temperature via plastic pipette; the liquid precipitated to a fluffy white solid. The mixture was stirred overnight before filtering over Whatman™ #4 and Sharkskin™ paper to give a fluffy off-white powder. The wet cake was dried under vacuum overnight at ambient temperature. Yield was 29.69 g (69.4%). HRMS: [M+Na]$^+$ calculated 841.6598, observed 841.6599; $^{31}$P NMR (CDCl$_3$) 4.31 ppm; $^1$H and $^{13}$C NMR consistent with desired structure.

Example 5

Preparation of Tetrapodal C$_{18}$-PEG$_{1000}$-OMe

Tetrakis(octadecyl)(((2,5,8,11,14,17,20,23,26,29,32,35, 38,41,44,47,50,53,56,59,62,65,68,71-tetracosaoxatriheptacontan-73-yl)azanediyl)bis(methylene))bis(phosphonate) (Referred to Herein as Tetrapodal C$_{18}$-PEG$_{1000}$-OMe)

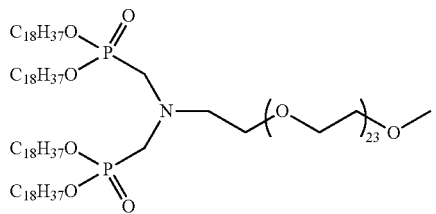

Figure 7:
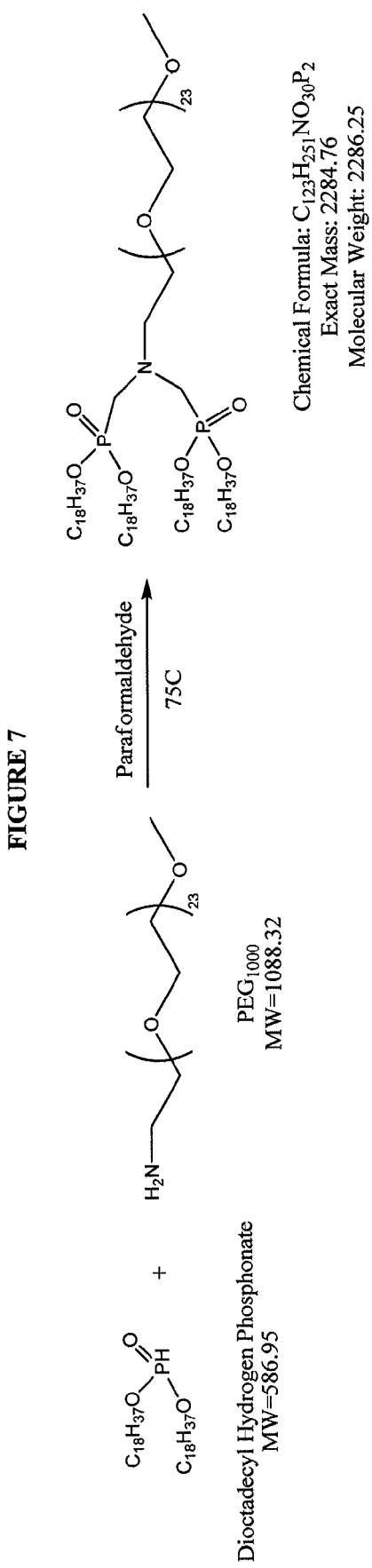
FIG. 7 shows a general reaction scheme for preparing a conjugate in accordance with an exemplary embodiment of the present invention.

FIG. 7 shows the general reaction scheme for preparing Tetrapodal C$_{18}$-PEG$_{1000}$-OMe, which was prepared by first making dioctadecyl hydrogen phosphonate as described in Example 2 above. Next, the Tetrapodal C$_{18}$-PEG$_{1000}$-OMe was produced as follows: A 10 mL Kontes microflex vial equipped with a triangular stirring vane was charged with dioctadecyl hydrogen phosphonate (1.0 g, 1.704 mmol, 2 eq.), paraformaldehyde (76.7 mg, 2.56 mmol, 3 eq.), and monodispersed PEG$_{1000}$ (Quanta Biodesign, 0.927 g, 0.852 mmol, 1 eq.). The cap was screwed on tightly and the vial was warmed to 75° C. and stirred for 24 to 72 hours. Periodically, the reaction was sampled for analysis using reverse phase (C4, 300 A) HPLC equipped with an evaporative light scattering detector (ELSD). If the reaction was deemed incomplete, additional paraformaldehyde may be added to aid in further conversion to the desired product. If the reaction has reached sufficient conversion to product, the reaction was cooled down and the resulting waxy solid was carried into purification.

The crude reaction material was dissolved in isopropyl alcohol using sonication and slight heating. The crude solution (typically 10-15 mg/mL) was purified by reverse phase chromatography on a Waters column (C4, 300 A, 5 μm, 19×150 mm) with a flow rate of 30 mL/min. The solvents used were acetonitrile (0.05% TFA) and water (0.05% TFA). Below is the gradient method used;

| Time | ACN (0.05% TFA) | Water (0.05% TFA) |
|---|---|---|
| 0 | 80 | 20 |
| 4 | 100 | 0 |
| 15 | 100 | 0 |
| 15.1 | 80 | 20 |
| 20 | 80 | 20 |

The fractions containing the desired product are reduced under vacuum and lyophilized to a solid (Isolated yield: 0.334 g, theoretical yield: 1.40 g, percent yield: 23.8%). LC/MS: [M+H]$^+$=2287.7 m/z. HPLC analysis using evaporative light scattering detection: 99 area percent. $^{31}$P NMR was consistent with the desired structure.

Example 6

Preparation of Tetrapodal C$_{18}$-PEG$_{2000}$-OMe

Tetrakis(octadecyl)-(2,5,8,11,14,17,20,23,26,29,32,35, 38,41,44,47,50,53,56,59,62,65,68,71,74,77,80,83,86,89, 92,95,98,101,104,107,110,113,116,119,122,125,128,131, 134-pentatetracontaoxahexatriacontahectan-136-yl azanediyl)bis(methylene)bis(phosphonate) (Referred to Herein as Tetrapodal C$_{18}$-PEG$_{2000}$-OMe)

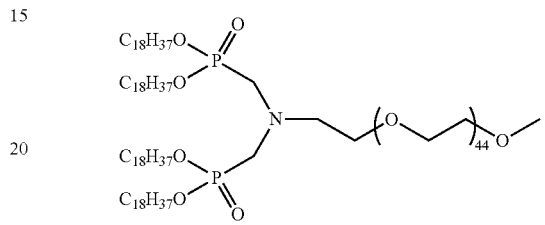

The synthetic steps for producing Tetrapodal C$_{18}$-PEG$_{2000}$-OMe were similar to those disclosed above in Example 5. First, dioctadecyl hydrogen phosphonate was prepared via the same method disclosed in Example 2. Next, Tetrapodal C$_{18}$-PEG$_{2000}$-OMe was produced as follows: A 10 mL Kontes microflex vial equipped with a triangular stirring vane was charged with dioctadecyl hydrogen phosphonate (0.587 g, 1.0 mmol, 2 eq.), paraformaldehyde (90.1 mg, 3.0 mmol, 6 eq.), and polydispersed PEG$_{2000}$ (NANOCS) (1.0 g, 0.50 mmol, 1 eq.). The cap was screwed on tightly and the vial was warmed to 75° C. and stirred for 24 to 72 hours. Periodically a small sample was withdrawn, dissolved in isopropanol (IPA)/water and analyzed using reverse phase (C4, 300 A) high performance liquid chromatograph (HPLC) equipped with an ELSD detector. If the reaction was deemed incomplete, additional paraformaldehyde may be added to aid in further conversion to the desired product. If the reaction has reached sufficient conversion to product, the reaction was cooled down and the resulting waxy solid was carried into purification.

The crude reaction material was dissolved in IPA/water (~3-5% water) using sonication and slight heating. The crude solution was typically 15-25 mg/mL. Desired product was obtained by reverse phase chromatography on a column containing C4 silica packing (5 μm, 300 Å). The solvents used were ACN (0.05% trifluoroacetic acid (TFA)) and water (0.05% TFA). Below is the gradient method used in conjunction with a Waters™ column (C4, 5 μm, 19×150 mm) with a flow rate of 30 mL/min:

| Time | ACN (0.05% TFA) | Water (0.05% TFA) |
|---|---|---|
| 0 | 80 | 20 |
| 4 | 100 | 0 |
| 15 | 100 | 0 |
| 15.1 | 80 | 20 |
| 20 | 80 | 20 |

The fractions containing the desired product are reduced under vacuum and isolated by lyophilization. Isolated yield (purified material): 0.335 g (20.8%). High Res. MS: Simulated Mass Spectrum [M+2Na]$^{2+}$=1628.1472; Detected Mass Spectrum [M+2Na]$^{2+}$=1628.1491. HPLC (ELSD): Single peak: Retention time (~7.88 minutes)=>98 area percent. LC/MS: [M+Na]$^{2+}$=1616.9 m/z. $^{31}$P NMR was consistent with the desired structure.

Example 7

Preparation of Tetrapodal $C_{14}$-$PEG_{1000}$-OMe

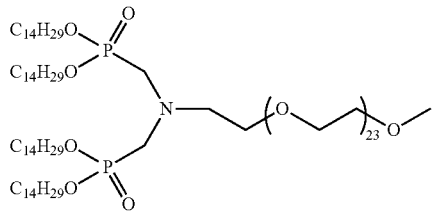

Tetrakis(tetradecyl) (((2,5,8,11,14,17,20,23,26,29,32,35,38,41,44,47,50,53,56,59,62,65,68,71-tetracosaoxatriheptacontan-73-yl)azanediyl)bis(methylene))bis(phosphonate) (Referred to Herein as Tetrapodal $C_{14}$-$PEG_{1000}$-OMe)

The procedure was the same as for Tetrapodal $C_{18}$-$PEG_{1000}$-OMe in Example 5, except that ditetradecyl hydrogen phosphonate was employed instead of dioctadecyl hydrogen phosphonate and the following amounts were used: ditetradecyl hydrogen phosphonate (0.404 g, 0.852 mmol, 2 eq.), paraformaldehyde (0.077 g, 2.56 mmol, 6 eq.), and monodispersed $PEG_{1000}$ (Quanta Biodesign™) (0.464 g, 0.426 mmol, 1 eq.). After reverse phase chromatography on a Waters™ column (C4, 300 A, 5 μm, 19×150 mm) the fractions containing the desired product were combined, reduced under vacuum, and lyophilized to a semi-solid; isolated yield 0.496 g (56.5%). HPLC analysis using ELSD detection: >99% by area. $^{31}P$ NMR was consistent with the desired structure.

Example 8

Preparation of other Tetrapodal Alkyl-PEG Phosphonate Conjugates

Other tetrapodal alkyl-PEG phosphonate conjugates can also be prepared. As set forth in general scheme in Example 1, dialkyl (e.g., $C_{12}$, $C_{16}$, and $C_{22}$) hydrogen phosphonates can be prepared. $C_{12}$-, $C_{16}$-, and $C_{22}$-$PEG_{1000}$-OMe phosphonate conjugates can then prepared using substantially the procedure described in Example 6. Instead of using 1-octadecanol, however, the reaction can include 1-dodecanol, 1-hexadecanol and 1-docosanol, respectively, for $C_{12}$-, $C_{16}$-, and $C_{22}$-$PEG_{1000}$-OMe conjugates, each of which is shown below. HRMS and/or LRMS and $^{31}P$ NMR were consistent with the desired structure of each of these derivatives.

Tetrakis(dodecyl)(((2,5,8,11,14,17,20,23,26,29,32,35,38,41,44,47,50,53,56,59,62,65,68,71-tetracosaoxatriheptacontan-73-yl)azanediyl)bis(methylene))bis(phosphonate) ($C_{12}$/$PEG_{1000}$ monodispersed). Chemical Formula: $C_{99}H_{203}NO_{30}P_2$, Molecular Weight: 1949.61 g/mol.

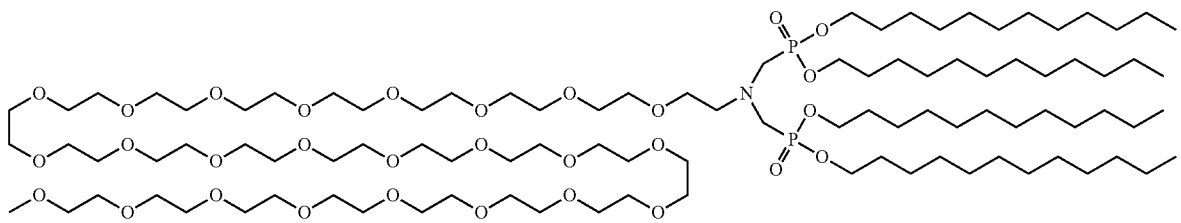 [SMILES: CCCCCCCCCCCCOP(=O)(CN(CCOCCOCCOCCOCCOCCOCCOCCOCCOCCOCCOCCOCCOCCOCCOCCOCCOCCOCCOCCOCCOCCOCCOCCOC)CP(=O)(OCCCCCCCCCCCC)OCCCCCCCCCCCC)OCCCCCCCCCCCC]

Tetrakis(hexadecyl)(((2,5,8,11,14,17,20,23,26,29,32,35,38,41,44,47,50,53,56,59,62,65,68,71-tetracosaoxatriheptacontan-73-yl)azanediyl)bis(methylene))bis(phosphonate) ($C_{16}$/$PEG_{1000}$ monodispersed). Chemical Formula: $C_{115}H_{235}NO_{30}P_2$, Molecular Weight: 2174.03 g/mol.

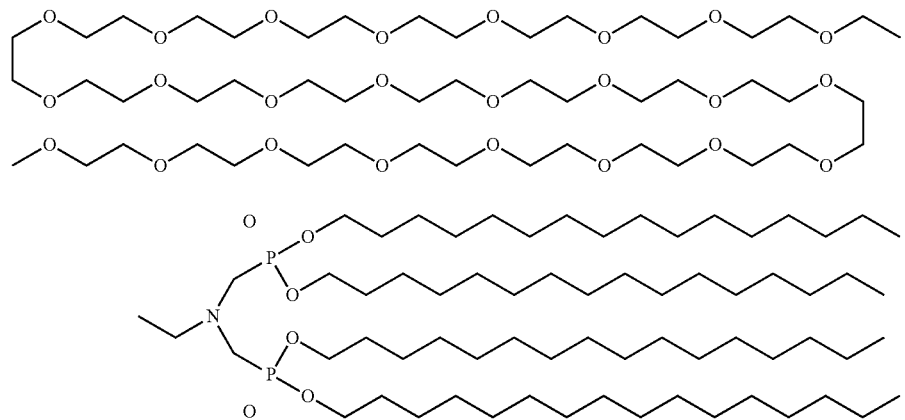

Tetrakis(docosyl)(((2,5,8,11,14,17,20,23,26,29,32,35,38,41,44,47,50,53,56,59,62,65,68,71-tetracosaoxatriheptacontan-73-yl)azanediyl)bis(methylene))bis(phosphonate) ($C_{22}$/$PEG_{1000}$ monodispersed). Chemical Formula: $C_{139}H_{283}NO_{30}P_2$, Molecular Weight: 2510.67 g/mol.

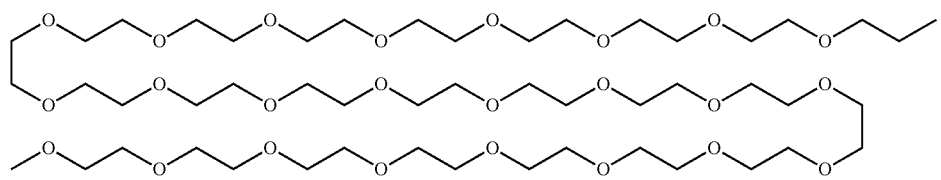

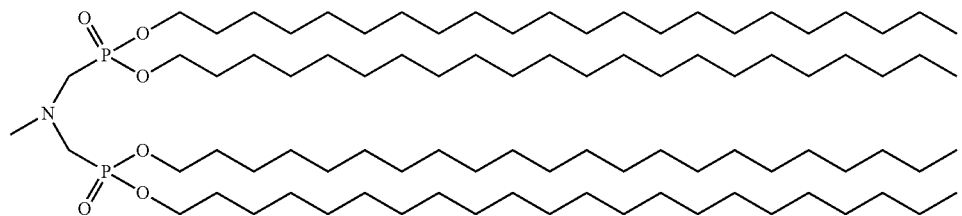

Similarly, conjugates having varying lengths of PEG molecules (e.g., $PEG_{100}$ to $PEG_{10000}$ or higher MW PEGs) can be prepared following some of the steps described above. For example, Tetrapodal $C_{18}$ phosphono-methyl amino-$PEG_{5000}$-OMe conjugates can be prepared following the steps in Example 6, except that polydispersed $PEG_{5000}$ is used instead of $PEG_{1000}$. The chemical structure for the Tetrapodal $C_{18}$ phosphono-methyl amino-$PEG_{5000}$-OMe conjugates is as follows:

Tetrakis(octadecyl)-(2,5,8,11,14,17,20,23,26,29,32,35, 38,41,44,47,50,53,56,59,62,65,68,71,74,77,80,83,86,89, 92,95,98,101,104,107,110,113,116,119,122,125,128,131, 134,137,140,143,146,149,152,155,158,161,164,167,170, 173,176,179,182,185,188,191,194,197,200,203,206,209, 212,215,218,221,224,227,230,233,236,239,242,245,248, 251,254,257,260,263,266,269,272,275,278,281,284,287, 290,293,296,299,302,305,308,311,314,317,320,323,326, 329,332,335,338,341,344,347-hexadecahectaoxapentacontatrictan-349-yl) azanediyl)bis(methylene)bis(phosphonate)

Chemical Formula: $C_{305}H_{615}NO_{121}P_2$, Exact Mass: 6291.15, Molecular Weight: 6295.03 g/mol.

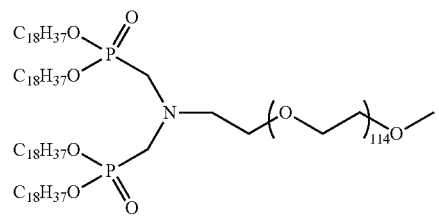

Example 9 di(2,5,8,11,14,17,20,23,26,29,32-undecaoxatetratriacontan-34-yl)phosphonate

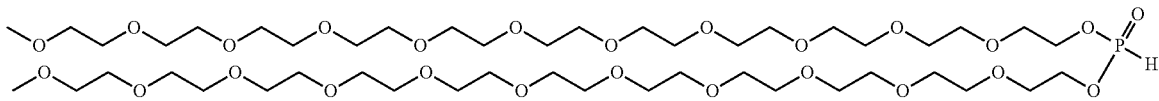 [SMILES: COCCOCCOCCOCCOCCOCCOCCOCCOCCOCCOCCO[PH](=O)OCCOCCOCCOCCOCCOCCOCCOCCOCCOCCOCCOC]

2,5,8,11,14,17,20,23,26,29,32-undecaoxatetratriacontan-34-ol (2.00 g, 3.87 mmol) was dissolved in toluene in a round bottom flask. The solution was dried by azeotropic distillation. The residual toluene was then stripped off. Pyridine (0.092 g, 1.16 mmol) and diphenylphosphite (0.45 g, 1.94 mmol) were then added. The mixture was heated at 65° C. for 16 hours. The reaction mixture was cooled to room temperature, dissolved in 15 mL dichloromethane, and stirred with 3.0 g of Dowex WBA resin for 30 minutes. The dichloromethane solution was filtered from the resin beads and volatiles evaporated to a yellow oil. The oil was dissolved in 1,2,4-trimethylbenzene and volatiles removed under reduced pressure azeotropically removing phenol by-product. Desired product (1.34 g) was obtained as an oil. HRMS: calculated: (M+2Na)/2=562.2842, (M+Na)=1101.5792, found: (M+2Na)/2=562.2818, (M+Na)=1101.5751. $^{31}P$ NMR: 9.22 ppm. $^{1}H$ NMR, $^{13}C$ NMR, and $^{13}C$ APT NMR are consistent with structure. Chemical Formula: $C_{46}H_{95}NO_{25}P$, Molecular Weight: 1078.59 g/mol.

Example 10

3-(((2-(bis((di(2,5,8,11,14,17,20,23,26,29,32-undecaoxatetratriacontan-34-yl)phosphoryl)methyl)amino)ethoxy)(hydroxy)phosphoryl)oxy)propane-1,2-diyl distearate

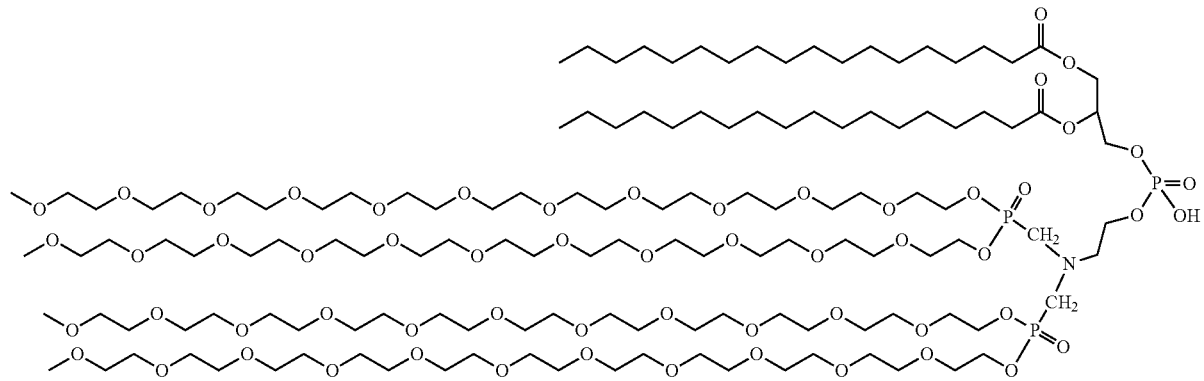 [SMILES: CCCCCCCCCCCCCCCCCC(=O)OCC(COP(=O)(O)OCCN(CP(=O)(OCCOCCOCCOCCOCCOCCOCCOCCOCCOCCOCCOC)OCCOCCOCCOCCOCCOCCOCCOCCOCCOCCOCCOC)CP(=O)(OCCOCCOCCOCCOCCOCCOCCOCCOCCOCCOCCOC)OCCOCCOCCOCCOCCOCCOCCOCCOCCOCCOCCOC)OC(=O)CCCCCCCCCCCCCCCCC]

DSPE (1,2-distearoyl-sn-glycero-3-phosphoethanolamine, 0.45 g, 0.60 mmol), di(2,5,8,11,14,17,20,23,26,29,32-undecaoxatetratriacontan-34-yl) phosphonate (1.34 g, 1.24 mmol) prepared in Example 9, paraformaldehyde (0.054 g, 1.81 mmol of formaldehyde), and dimethylformamide (2.0 mL) were added to a scintillation vial. The vial was capped and heated at 75° C. for 24 hours. The reaction mixture was stripped, dissolved in methanol and treated with Dowex WBA resin (1.0 g). The methanol solution was filtered from the resin beads and stripped to a yellow oil. The oil was dissolved in 15 mL of 80/20 water/isopropyl alcohol and chromatographed through a column, loaded with Grace Vydac Protein C-4 reverse phase packing, using a water/isopropyl alcohol eluent. The desired fractions were frozen and lyophilized to yield 0.337 g of the target compound as a white powder. LRMS found: (M+2H)/2=1465, (M+2Na)/2=1487, (M+3H)/3=977. HRMS: calculated: (M−H) 2927.7505, found: (M−H) 2927.7570. $^{31}$P NMR found 25.96 ppm and −0.21 ppm. $^1$H NMR, $^{13}$C NMR, and $^{13}$C APT NMR are consistent with structure. HPLC analysis (ELSD) found 99.8 area % for the desired product peak. Chemical Formula: $C_{135}H_{272}NO_{58}P_3$, Molecular Weight: 2928.76 g/mol.

Example 11

Tetraphenyl-(2-methoxyethylazanediyl)bis(methylene)diphosphonate. Chemical Formula: $C_{29}H_{31}NO_7P_2$, Exact Mass: 567.16, Molecular Weight 567.51 g/mol

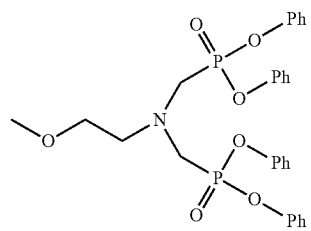 [SMILES: COCCN(CP(=O)(Oc1ccccc1)Oc1ccccc1)CP(=O)(Oc1ccccc1)Oc1ccccc1]

This compound was prepared using the following procedure. 2-methoxyethylamine (3 g, 40 mmol; 3.44 mL) was combined with formaldehyde (2.4 g; 320 mmol, 6.5 mL of 37% in $H_2O$) and dimethylformamide (DMF) (30 mL). Diphenylphosphite (DPP) (20.6 g, 88 mmol; 2.2 equiv.) was added to the mixture slowly. After a short initial exothermic reaction, the mixture was stirred for 12 hours at room temperature. HPLC indicated complete reaction and then DMF was evaporated. The residue was dissolved in ethyl acetate (EA) (200 mL) and washed with sat. $KHSO_4$ and brine. The layers were separated and the organic layer was dried over Na2SO4, filtered and volatiles removed under vacuum on a rotary evaporator. The residual oil was dissolved in EA/hexane mixture (1:4) and filtered through a silica plug. Then the product was eluted off the silica with EA/hexane mixture (1:1). The solvent was evaporated, yielding 15.6 g (27 mmol; 69%) as a clear oil. LC/MS: MH+=568.2 $^1$H and $^{31}$P NMR consistent with structure.

Example 12

Tetraoctadecyl-(2-methoxyethylazanediyl)bis(methylene)diphosphonate. Chemical Formula: $C_{77}H_{159}NO_7P_2$, Exact Mass: 1272.16, Molecular Weight: 1273.04 g/mol

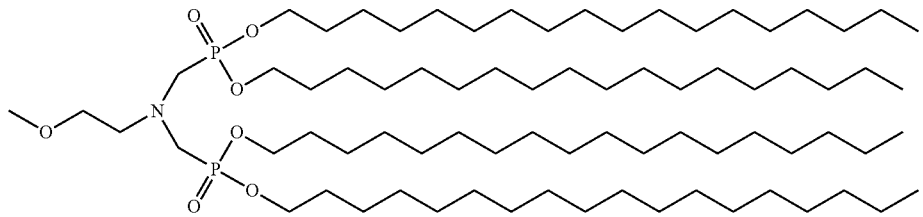 [SMILES: CCCCCCCCCCCCCCCCCCOP(=O)(CN(CCOC)CP(=O)(OCCCCCCCCCCCCCCCCCC)OCCCCCCCCCCCCCCCCCC)OCCCCCCCCCCCCCCCCCC]

This molecule was prepared using substantially the procedure of Example 11, but ditetradecyl hydrogen phosphonate was employed in place of diphenylphosphite (DPP) and the reaction was run without DMF solvent (i.e. solvent free) as in Example 5 using a reaction vial (10 mL) and teflon coated spin vane with a work-up and isolation as described in Example 5.

Example 13

3-(bis((bis(octadecyloxy)phosphoryl)methyl)amino)propanoic acid. Chemical Formula: $C_{77}H_{157}NO_8P_2$, Exact Mass: 1286.14, Molecular Weight 1287.02 g/mol

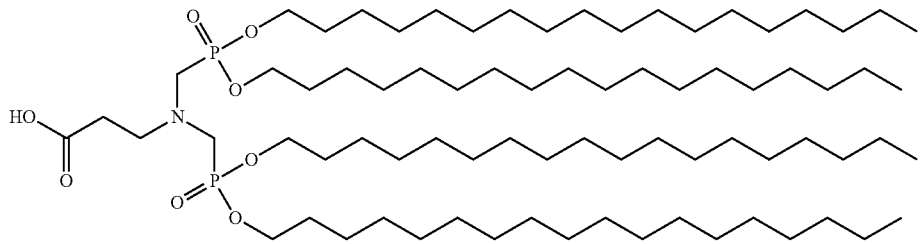 [SMILES: CCCCCCCCCCCCCCCCCCOP(=O)(CN(CCC(=O)O)CP(=O)(OCCCCCCCCCCCCCCCCCC)OCCCCCCCCCCCCCCCCCC)OCCCCCCCCCCCCCCCCCC]

This compound was prepared as follows: Dioctadecyl phosphonate (5.87 g, 10 mmol) was reacted with β-alanine (0.45 g, 5 mmol) and formaldehyde (6 mL of 37% solution in water) in DMF (20 mL) at 80° C. with stirring for 2 days in a pressure bottle. The reaction mixture was removed and volatiles were evaporated carefully and the residue was dissolved in $CHCL_3$ (200 mL). The organic layer was washed with 10% $KHSO_4$ and brine (50 ml each). The organic phase was dried over $MgSO_4$, filtered and evaporated to an oil. The remaining oil was mixed with ~100 mL acetone after a few hours stirring, the fine white precipitate was filtered off. Yield: 5.4 g (4.2 mmol: 84%) as crude. $^{31}P$ NMR 24.503 ppm. HRMS: calculated $MH^+$ 1287.1384; actual $MH^+$=1287.1477.

Example 14

2-(bis((bis(octadecyloxy)phosphoryl)methyl)amino)acetic acid. Chemical Formula: $C_{76}H_{155}NO_8P_2$, Exact Mass: 1272.12, Molecular Weight: 1272.99 g/mol

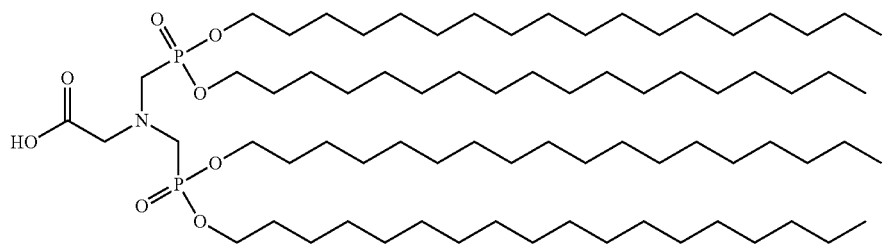 [SMILES: CCCCCCCCCCCCCCCCCCOP(=O)(CN(CC(=O)O)CP(=O)(OCCCCCCCCCCCCCCCCCC)OCCCCCCCCCCCCCCCCCC)OCCCCCCCCCCCCCCCCCC]

This compound was prepared by reacting dioctadecyl phosphonate with glycine and formaldehyde in DMF, similar to Example 13. The product was isolated in a similar manner as shown in Example 13. The structure was confirmed by $^{31}$P NMR and HRMS.

Example 15

Tetraoctadecyl (78-methyl-75-oxo-2,5,8,11,14,17,20,23,26,29,32,35,38,41,44,47,50,53,56,59,62,65,68,71-tetracosaoxa-74,78-diazanonaheptacontan-79-yl)bis(methylene) diphosphonate. Chemical Formula: $C_{126}H_{256}N_2O_{31}P_2$, Molecular Weight: 2357.32 g/mol

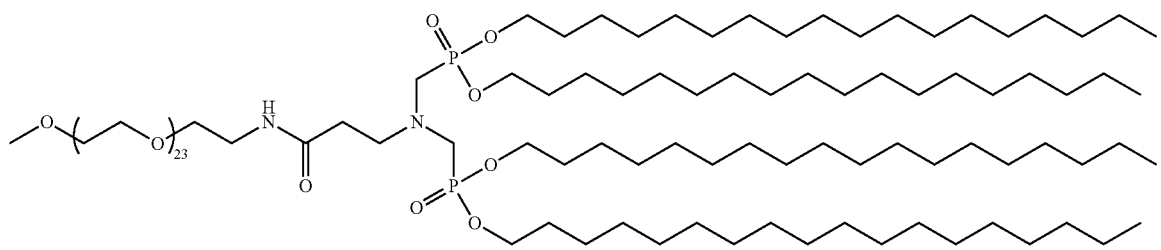

Figure 8:
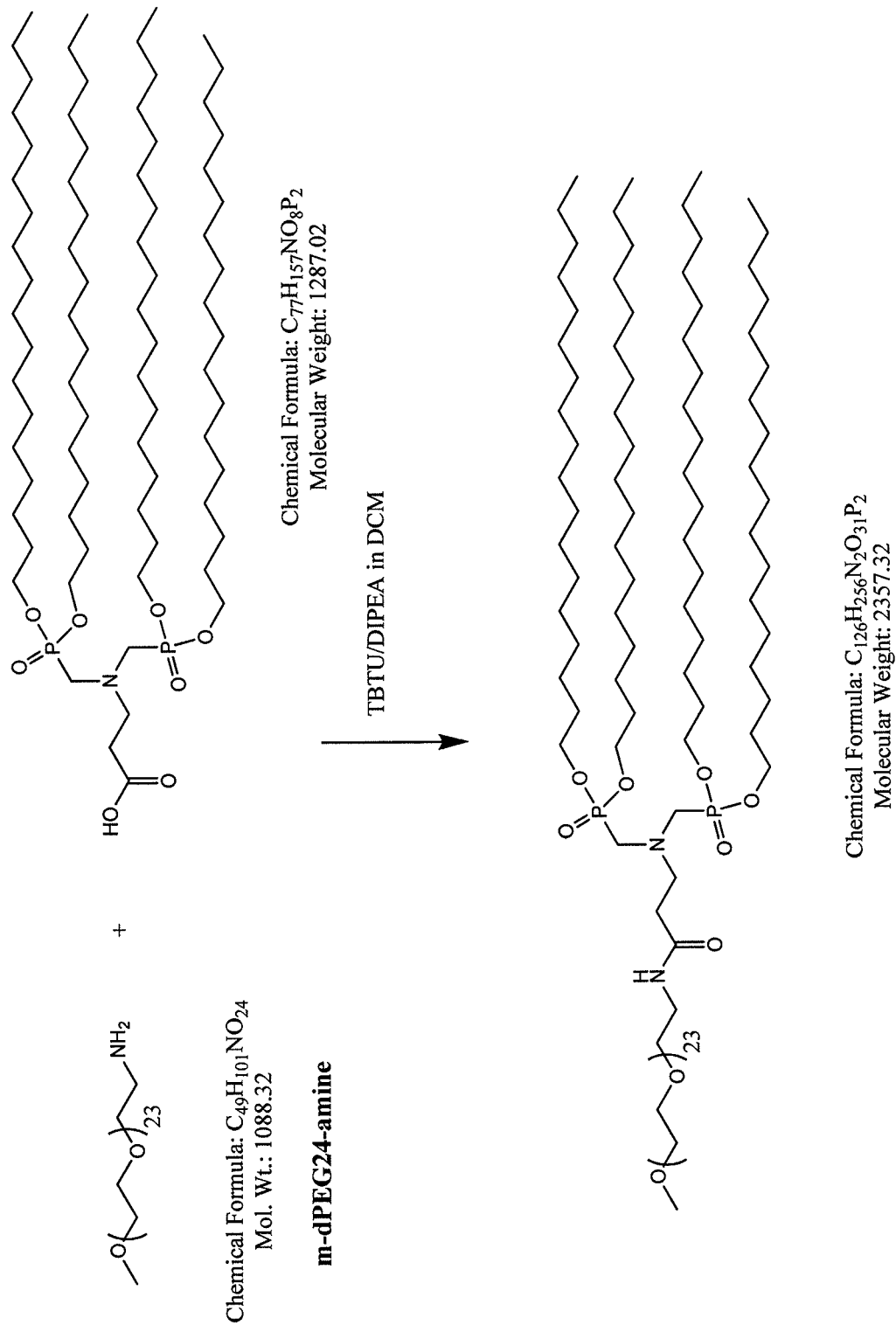
FIG. 8 shows another general reaction scheme for preparing a conjugate in accordance with an exemplary embodiment of the present invention.

3-(bis((bis(octadecyloxy)phosphoryl)methyl)amino)propanoic acid (128 mg, 0.1 mmol) was coupled with m-dPEG$_{24}$-amine (108 mg, 0.1 mmol) in DCM (20 mL) in the presence of TBTU (O-(Benzotriazol-1-yl)-N,N,N',N-tetramethyluronium tetrafluoroborate) (48 mg, 0.15 mmol) and DIPEA (N,N-Diisopropylethylamine) (0.175 mL). (See FIG. 8). After stirring for 12 hours at room temperature, the mixture was diluted with dichloromethane (DCM) (100 mL) and washed with 10% KHSO$_4$ and brine. DCM solution was dried over Na$_2$SO4, filtered and the solvent was evaporated to yield 220 mg clear oil (as crude material) that could be purified by C4, 300 A rphplc and lyophilized to give the desired product. MS: M+Na$^+$=2,379.73 and $^{31}$P NMR consistent with structure.

Example 16

Dioctadecyl (78-methyl-75-oxo-2,5,8,11,14,17,20,23,26,29,32,35,38,41,44,47,50,53,56,59,62,65,68,71-tetracosaoxa-74,78-diazanonaheptacontan-79-yl) phosphonate (C$_{18}$/N-methyl beta-alanine/PEG$_{1000}$). Chemical Formula: $C_{90}H_{183}N_2O_{28}P$, Exact Mass: 1771.27, Molecular Weight: 1772.39 g/mol

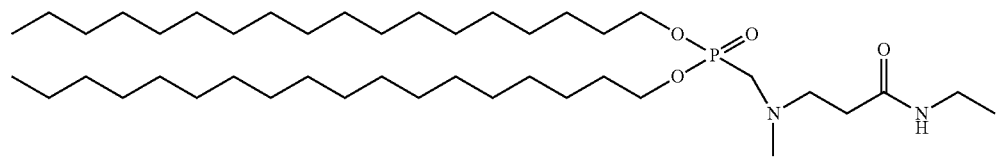

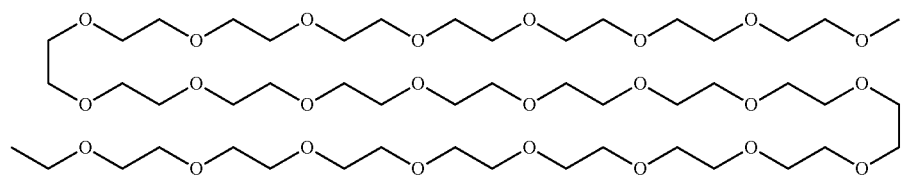

This compound can be synthesized by reacting 3-(bis((bis(octadecyloxy)phosphoryl)methyl)amino)propanoic acid formed in Example 13 with m-dPEG$_{24}$-amine in the presence of TBTU using substantially the same reaction conditions and purification procedures outlined in Example 15.

Example 17

Dioctadecyl (78-carboxyl-75-oxo-2,5,8,11,14,17,20,23,26,29,32,35,38,41,44,47,50,53,56,59,62,65,68,71-tetracosaoxa-74,78-diazanonaheptacontan-79-yl) phosphonate ($C_{18}$/N-methyl beta-alanine/PEG$_{1000}$ carboxylate) Chemical Formula: $C_{92}H_{185}N_2O_{30}P$, Exact Mass: 1829.27, Molecular Weight: 1830.42 g/mol

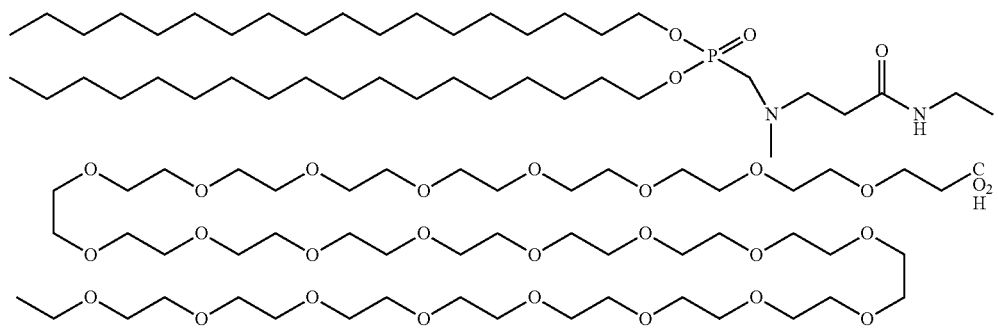

This compound may be synthesized by reacting 3-(bis((bis(octadecyloxy)phosphoryl)methyl)amino)propanoic acid formed in Example 13 with amino-PEG$_{24}$-caboxylate ester in the presence of TBTU using substantially the same reactions conditions and purification procedures outlined in Example 15 to obtain the ester. Hydrolysis of the ester to the acid may be achieved under basic or acidic conditions and the product carboxylate isolated by C4 reverse phase HPLC, combining like fractions and lyophilizing to obtain substantially pure product.

Example 18

Dioctadecyl 158-methyl-77,155-dioxo-2,4,7,10,13,16,19,22,25,28,31,34,37,40,43,46,49,52,55,58,61,64,67,70,73,80,82,85,88,91,94,97,100,103,106,109,112,115,118,121,124,127,130,133,136,139,142,145,148,151-pentacontaoxa-76,154,158-triazanonapentacontahectan-159-ylphosphonate ($C_{18}$/N-methyl beta-alanine/PEG$_{1000}$ amide linked PEG$_{1000}$)

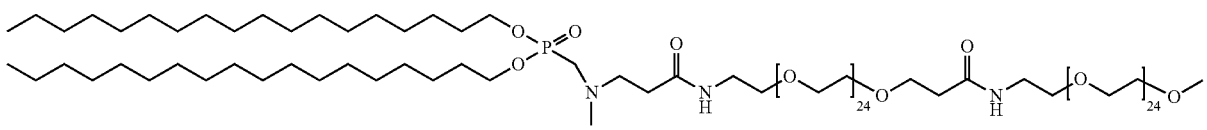

This compound may be prepared by taking the product of Example 15 and reacting it with amino-PEG OMe (1000 MW) using substantially the coupling procedure and purification scheme of Example 15.

Example 19

2-(((bis((3S,8S,9S,10R,13R,14S,17R)-10,13-dimethyl-17-(R)-6-methylheptan-2-yl)-2,3,4,7,8,9,10,11,12,13,14,15,16,17-tetradecahydro-1H-cyclopenta[a]phenanthren-3-yloxy)phosphoryl)methyl)(methyl)amino)acetic acid (Dicholesterol/Sarcosine). Chemical Formula: $C_{58}H_{98}NO_5P$, Exact Mass: 919.72, Molecular Weight: 920.38 g/mol

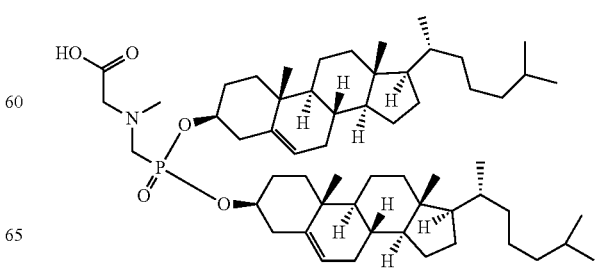

This compound was prepared as follows: Dicholesteryl hydrogen phosphonate (5.0 g, 0.006 mol) was reacted with sarcosine (0.54 g, 0.006 mol) and formaldehyde (2.2 g, 0.03 mol) in DMF at 75° C. as a heterogeneous mixture. After 4 hours at 75° C., a 9% conversion to desired dicholesterolphosphonyl methyl sarcosine was obtained. Another portion of formaldehyde (2.2 g, 0.03 mol) was added and the reaction temperature increased to 85° C. After 16 hours at 85° C., a 55% conversion to desired 2-(((bis((3S,8S,10R,13R,17R)-10,13-dimethyl-17-((R)-6-methylheptan-2-yl)-tetradecahydro-2,3,4,7,8,9,10,11,12,13,14,15,16,17 1H-cyclopenta[a]phenanthren-3-yloxy)phosphoryl)methyl)(methyl)amino)acetic acid was obtained and a yellow solid that precipitated from the reaction mixture upon cooling. The product was isolated by filtration (yellow solid) and identity confirmed by $^{31}$P NMR (22.5 ppm). Crude Dipodal Cholesterol Sarcosine (700 mg) was purified on silica gel (15 g) using 95% chloroform/5% MeOH.

Example 20

2-(((bis(octadecyloxy)phosphoryl)methyl)(methyl)amino)acetic acid ($C_{18}$/Sarcosine). Chemical Formula: $C_{40}H_{82}NO_5P$, Exact Mass: 687.59, Molecular Weight: 688.06 g/mol

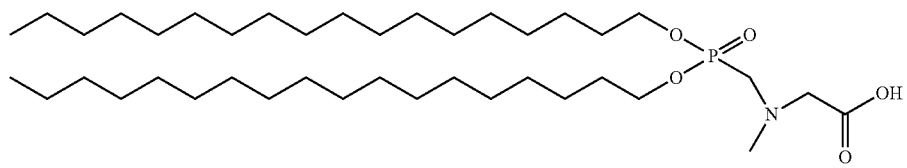 [SMILES: CCCCCCCCCCCCCCCCCCOP(=O)(CN(C)CC(=O)O)OCCCCCCCCCCCCCCCCCC]

This compound was prepared as follows: To a RBF (250 mL) equipped with mechanical stirrer and thermocouple were added dioctadecyl hydrogen phosphonate (1.98 g 0.003 mol), sarcosine (0.30 g, 0.003 mol) and of formaldehyde (1.1 g, 0.013 mol) in N,N-dimethylformamide (50 mL) at 75° C. After 2 hours, a 76% conversion to 2-((bis(octadecyloxy)phosphoryl)(methyl)amino)acetic acid was observed by $^{31}$P NMR (24.4 ppm). The reaction was allowed to continue for another 4 hours at 75° C. producing an 88.5% conversion. At this point the reaction mixture was allowed to cool to ambient temperature and a pale orange slurry was obtained. Water (50 mL) was added and the mixture stirred for an additional 30 minutes at ambient temperature. The product was isolated as a pale orange solid by filtration. The solid was dried in an oven at 30-40° overnight (2.0 g). A final purity of 81.3% of the Dipodal C18 Sarcosine was confirmed on the isolated solids by $^{31}$P NMR (24.3 ppm). HPLC-MS (689.6 M+H$^+$). $^{13}$C and $^1$H NMR were consistent with the assigned structure.

Example 21

3-(((bis(octadecyloxy)phosphoryl)methyl)(methyl)amino)propanoic acid ($C_{18}$/N-methyl beta-alanine). Chemical Formula: $C_{41}H_{84}NO_5P$, Exact Mass: 701.61, Molecular Weight: 702.08 g/mol

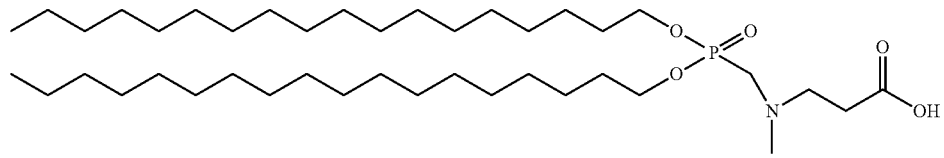 [SMILES: CCCCCCCCCCCCCCCCCCOP(=O)(CN(C)CCC(=O)O)OCCCCCCCCCCCCCCCCCC]

This compound was prepared using substantially the same procedure as in Example 20 but methyl beta-alanine was substituted for sarcosine. After C4 reverse HPLC purification and isolation, the expected MS and $^{31}$P NMR was obtained.

Example 22

2-(((bis((Z)-octadec-9-enyloxy)phosphoryl)methyl)(methyl)amino)acetic acid ($C_{18}$ Oleyl/Sarcosine). Chemical Formula: $C_{40}H_{78}NO_5P$, Exact Mass: 683.56, Molecular Weight: 684.02 g/mol

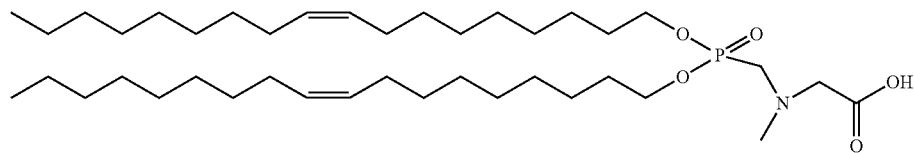 [SMILES: CCCCCCCC/C=C\CCCCCCCCOP(=O)(CN(C)CC(=O)O)OCCCCCCCC/C=C\CCCCCCCC]

This compound was prepared as follows: To a RBF (250 mL) equipped with mechanical stirrer and thermocouple were added dioleyl hydrogen phosphonate (1.96 g, 0.003 mol), sarcosine (0.30 g, 0.003 mol) and formaldehyde (1.1 g, 0.013 mol) in N,N-dimethylformamide (50 mL) at 75° C. The reaction was allowed to take place for 4 hours at 75° C. An approximate 89% conversion to desired 2-((bis((Z)-octadec-9-enyloxy)phosphoryl)(methyl)amino)acetic acid was observed with $^{31}$P NMR ~24 ppm. Allowed reaction mixture to cool to ambient temperature overnight and then evaporated to an oil. Product was confirmed with $^{13}$C and $^{1}$H NMR and LCMS.

Example 23

2-((1-(bis(octadecyloxy)phosphoryl)-3-ethoxy-3-oxoethyl)(methyl)amino)acetic acid. Chemical Formula: $C_{43}H_{86}NO_7P$, Exact Mass: 759.61419, Molecular Weight: 760.12 g/mol

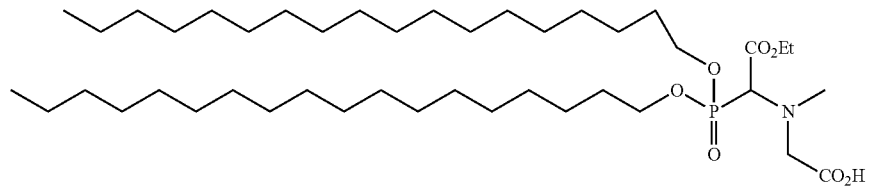 [SMILES: CCCCCCCCCCCCCCCCCCOP(=O)(OCCCCCCCCCCCCCCCCCC)C(C(=O)OCC)N(C)CC(=O)O]

In a 25 mL round-bottomed flask, sarcosine (0.21 g, 2.3 mmol), dioctadecyl hydrogen phosphonate (0.69 g, 1.2 mmol), 1-octadecanol (0.63 g, 2.3 mmol) and ethyl glyoxalate (0.36 g, 1.8 mmol) in 4 mL toluene and 4 mL dimethyl sulfoxide was stirred at 100° C. for 16 h under argon. Reaction mixture in $CDCl_3$ was checked by $^{31}$P NMR indicating presence of significant desired product (24.8 ppm). The reaction mixture was purified by normal phase flash chromatography using a gradient of chloroform/isopropanol containing 5% ammonium hydroxide and desired 2-((1-(bis(octadecyloxy)phosphoryl)-3-ethoxy-3-oxoethyl)(methyl)amino)acetic acid obtained.

Example 24

2-(((bis(octadecyloxy)phosphoryl)(phosphono)methyl)(methyl)amino) acetic acid. Chemical Formula: $C_{40}H_{83}NO_8P_2$, Molecular Weight: 768.04 g/mol

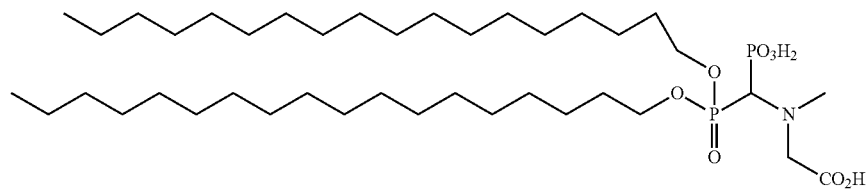

The title compound may be prepared by following substantially the procedure of Example 23 but substituting formyl phosphonic acid (Wagenknecht, J. H., Journal of the Electrochemical Society (1976), 123(5), 620-4, U.S. Pat. No. 4,568,432, and WO9850391) for ethyl glyoxylate in similar proportions.

What is claimed is:

1. A compound of the formula:

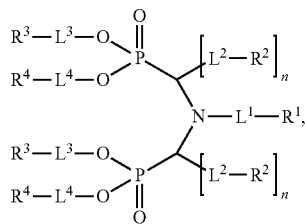

wherein
each $L^1$, $L^2$, $L^3$ and $L^4$ is independently selected from the group consisting of a bond and a linking group;
$R^1$ is selected from the group consisting of a nanoparticle, an attachment component, a targeting agent, a diagnostic agent, a stealth agent, and a tetrapodal presentation component;
each $R^2$ is independently selected from the group consisting of a stealth agent, $C_1$-$C_{10}$ alkyl, a carboxylic acid or ester, a phosphonic acid or ester, a sulfonic acid or ester, and a hydroxy;
each $R^3$ and $R^4$ is independently selected from the group consisting of H, a nanoparticle, an attachment component, a targeting agent, a diagnostic agent, and a stealth agent, wherein at least one of $R^3$ or $R^4$ is other than H; and
n is an integer of from 0 to 2.

2. The compound of claim 1, wherein at least one of $L^1$, $L^2$, $L^3$, and $L^4$ is a hydrophilic, non-immunogenic, water soluble linking group.

3. The compound of claim 2, wherein the hydrophilic, non-immunogenic, water soluble linking group is selected from the group consisting of polyethylene glycol, polypropylene glycol, polyvinyl alcohol, polycarboxylate, polysaccharide and dextran.

4. The compound of claim 1, wherein the targeting agent is an aptamer.

5. The compound of claim 1, wherein the diagnostic agent is a radioactive agent, a fluorescent agent, or a contrast agent.

6. The compound of claim 1, wherein the stealth agent is selected from the group consisting of a dendrimer, polyalkylene oxide, polyvinyl alcohol, polycarboxylate, a polysaccharide and hydroxyalkyl starch.

7. The compound of claim 6, wherein the stealth agent is a polyalkylene oxide.

8. The compound of claim 7, wherein the polyalkylene oxide is a polyethylene glycol (PEG) ranging from $PEG_{100}$ to $PEG_{10000}$.

9. The compound of claim 6, wherein the polyalkylene oxide is polyethylene glycol (PEG) selected from the group consisting of $PEG_{100}$, $PEG_{500}$, $PEG_{1000}$, $PEG_{2000}$, $PEG_{5000}$ and $PEG_{10000}$.

10. The compound of claim 1, wherein the stealth agent comprises at least two PEG molecules linked together with a linking group.

11. The compound of claim 1, wherein $R^1$ is a tetrapodal presentation component having the formula:

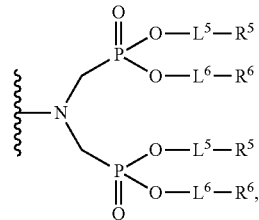

wherein
each $L^5$ and $L^6$ is independently selected from the group consisting of a bond and a linking group; and
each $R^5$ and $R^6$ is independently selected from the group consisting of a targeting agent, a diagnostic agent, and a stealth agent.

12. The compound of claim 1, wherein each of $R^3$ and $R^4$ is independently selected from the group consisting of a lipid and cholesterol.

13. The compound of claim 1, wherein $R^1$ is a stealth agent; and each of $R^3$ and $R^4$ is an attachment component and independently selected from the group consisting of a lipid and cholesterol, wherein the attachment component is attached to a nanoparticle.

14. The compound of claim 13, wherein the lipid is saturated or unsaturated $C_{10}$-$C_{22}$ alkyl.

15. The compound of claim 14, wherein n is 0.

16. The compound of claim 1, wherein $R^1$ is an attachment component; and $R^3$ and $R^4$ are independently selected from the group consisting of a targeting agent, a diagnostic agent and a stealth agent.

17. The compound of claim 1, wherein $R^1$ is a stealth agent selected from the group consisting of $PEG_{100}$, $PEG_{500}$, $PEG_{1000}$, $PEG_{2000}$, $PEG_{5000}$ and $PEG_{10000}$.

18. The compound of claim 1, wherein $R^1$ is an attachment component, and the attachment component is a phospholipid.

19. The compound of claim 18, wherein the phospholipid has the formula:

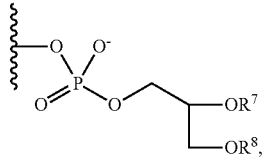

wherein each of $R^7$ and $R^8$ is independently selected from the group consisting a saturated or unsaturated $C_{10-24}$ alkyl or alkanoyl group and a substituted saturated or unsaturated $C_{10-24}$ alkyl or alkanoyl group.

20. The compound of claim 1, wherein each $R^1$ and $R^2$ is a stealth agent; each $R^3$ and $R^4$ is an attachment component independently selected from the group consisting of a lipid and cholesterol; and n is 1.

* * * * *